(12) United States Patent
Marashdeh et al.

(10) Patent No.: US 10,194,826 B2
(45) Date of Patent: *Feb. 5, 2019

(54) ADAPTIVE ELECTRICAL CAPACITANCE VOLUME TOMOGRAPHY

(71) Applicant: Ohio State Innovation Foundation, Columbus, OH (US)

(72) Inventors: Qussai Mohammad Marashdeh, Columbus, OH (US); Liang-Shih Fan, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 474 days.

This patent is subject to a terminal disclaimer.

(21) Appl. No.: 14/988,075

(22) Filed: Jan. 5, 2016

(65) Prior Publication Data

US 2016/0206227 A1    Jul. 21, 2016

Related U.S. Application Data

(63) Continuation of application No. 13/644,973, filed on Oct. 4, 2012, now Pat. No. 9,259,168.

(60) Provisional application No. 61/543,233, filed on Oct. 4, 2011.

(51) Int. Cl.
*A61B 5/05* (2006.01)
*A61B 5/053* (2006.01)

(52) U.S. Cl.
CPC ............. *A61B 5/0536* (2013.01); *A61B 5/05* (2013.01); *A61B 2562/0214* (2013.01); *A61B 2562/046* (2013.01)

(58) Field of Classification Search
USPC .................................................. 324/660–690
See application file for complete search history.

(56) References Cited

U.S. PATENT DOCUMENTS

| | | | |
|---|---|---|---|
| 5,130,661 A * | 7/1992 | Beck | G01N 27/226 324/663 |
| 5,365,560 A | 11/1994 | Tam | |
| 7,496,450 B2 | 2/2009 | Ortiz Aleman et al. | |
| 7,840,053 B2 | 11/2010 | Liao | |
| 8,116,430 B1 | 2/2012 | Shapiro et al. | |
| 8,508,238 B2 | 8/2013 | Mahalingam et al. | |
| 9,259,168 B2 | 2/2016 | Marashdeh et al. | |

(Continued)

FOREIGN PATENT DOCUMENTS

| | | |
|---|---|---|
| GB | 2302408 A | 1/1997 |
| GB | 2390683 A | 1/2004 |
| WO | 2010007096 A2 | 1/2010 |

OTHER PUBLICATIONS

Hua et al, Three Dimensional Analysis of Electrical Capacitance Tomography Sensing Fields, 1999 IOP Publishing LTD, vol. 10, pp. 717-725.

(Continued)

*Primary Examiner* — Vincent Q Nguyen
(74) *Attorney, Agent, or Firm* — Standley Law Group LLP

(57) ABSTRACT

An electrical capacitance tomography sensor including a sensor having a plurality of electrodes, where each electrode is formed from a plurality of capacitance segments. Each of the capacitance segments of each electrode can be individually addressed to focus the electric field intensity or sensitivity to desired regions of the electrodes and the sensor.

29 Claims, 35 Drawing Sheets

(56) References Cited

U.S. PATENT DOCUMENTS

| | | |
|---|---|---|
| 2003/0031291 A1 | 2/2003 | Yamamoto et al. |
| 2004/0028181 A1 | 2/2004 | Charles, Jr. et al. |
| 2004/0233191 A1 | 11/2004 | Mukherjee et al. |
| 2007/0186679 A1 | 8/2007 | Zangl et al. |
| 2008/0247502 A1 | 10/2008 | Liao |
| 2009/0160461 A1 | 6/2009 | Zangl et al. |
| 2010/0097374 A1 | 4/2010 | Fan et al. |
| 2010/0148804 A1* | 6/2010 | Jakoby .................. G01F 1/662 324/663 |
| 2010/0332170 A1 | 12/2010 | Gao et al. |
| 2011/0074058 A1 | 3/2011 | Lederer et al. |
| 2013/0049770 A1 | 2/2013 | Basu et al. |

OTHER PUBLICATIONS

Marashdeh, Q., Advances in Electrical Capacitance Tomography, Dissertation, The Ohio State University, 2006.

Marashdeh, Q. et al., On the ECT Sensor Based Dual Imaging Modality System for Electrical Permittivity and conductivity Measurements, 2006, pp. 1-6, The Ohio State University, Columbus, Ohio.

Narsito, W. et al., Electrical Capacitance Volume Tomography, 2007, pp. 1-9.

* cited by examiner

CASES 1&2: PARALLEL PLATE ARRANGEMENT
CASE 1: Vp1 = Vp2 = Vp3 = Vp4 = +5Volts; Vn1 = Vn2 = Vn3 = Vn4 = -5Volts
CASE 2: Vp1 = +1, Vp2 = +2, Vp3 = +4, Vp4 = +7; Vn1 = -1, Vn2 = -2, Vn3 = -4, Vn4 = -7

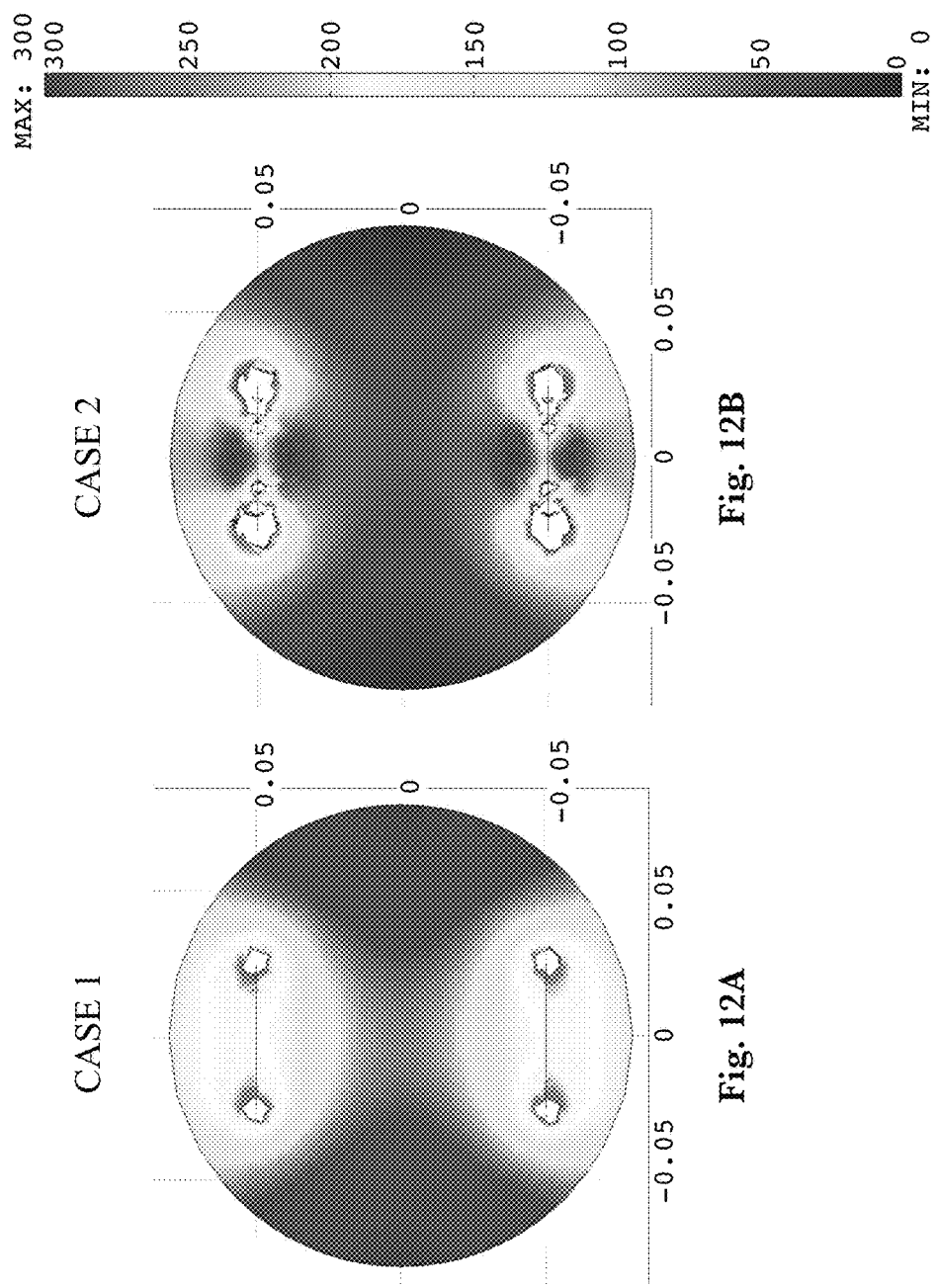

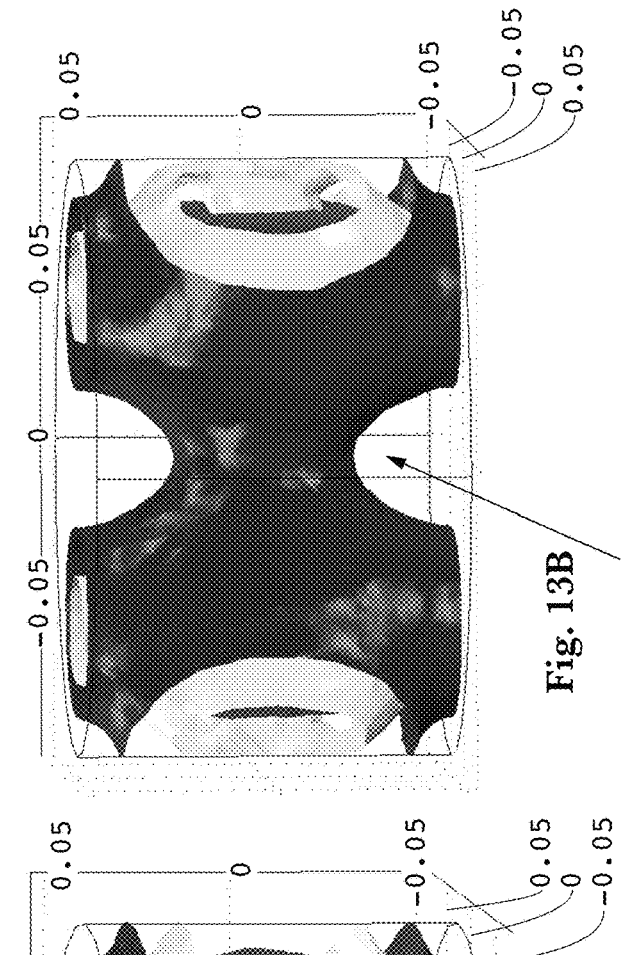
Fig. 13A CASE 1
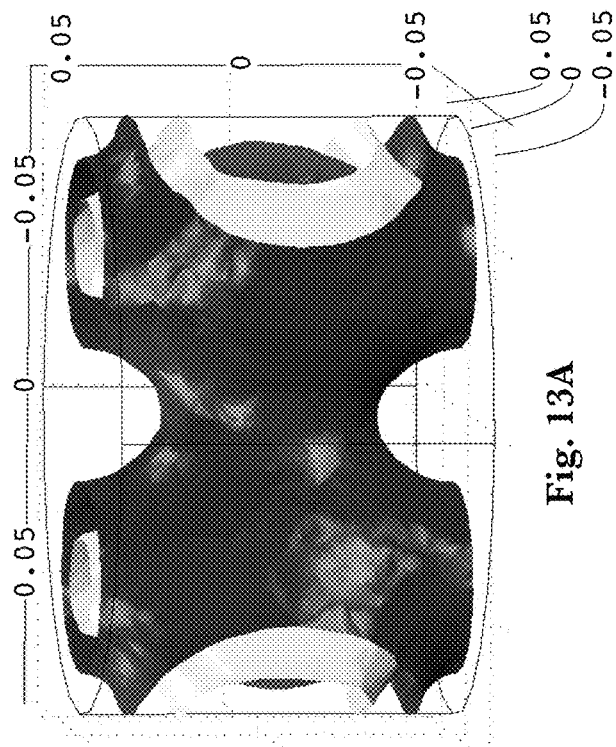
Fig. 13B CASE 2
GAP IS BIGGER FOR CASE 2: ELECTRIC FIELD IS MORE FOCUSSED

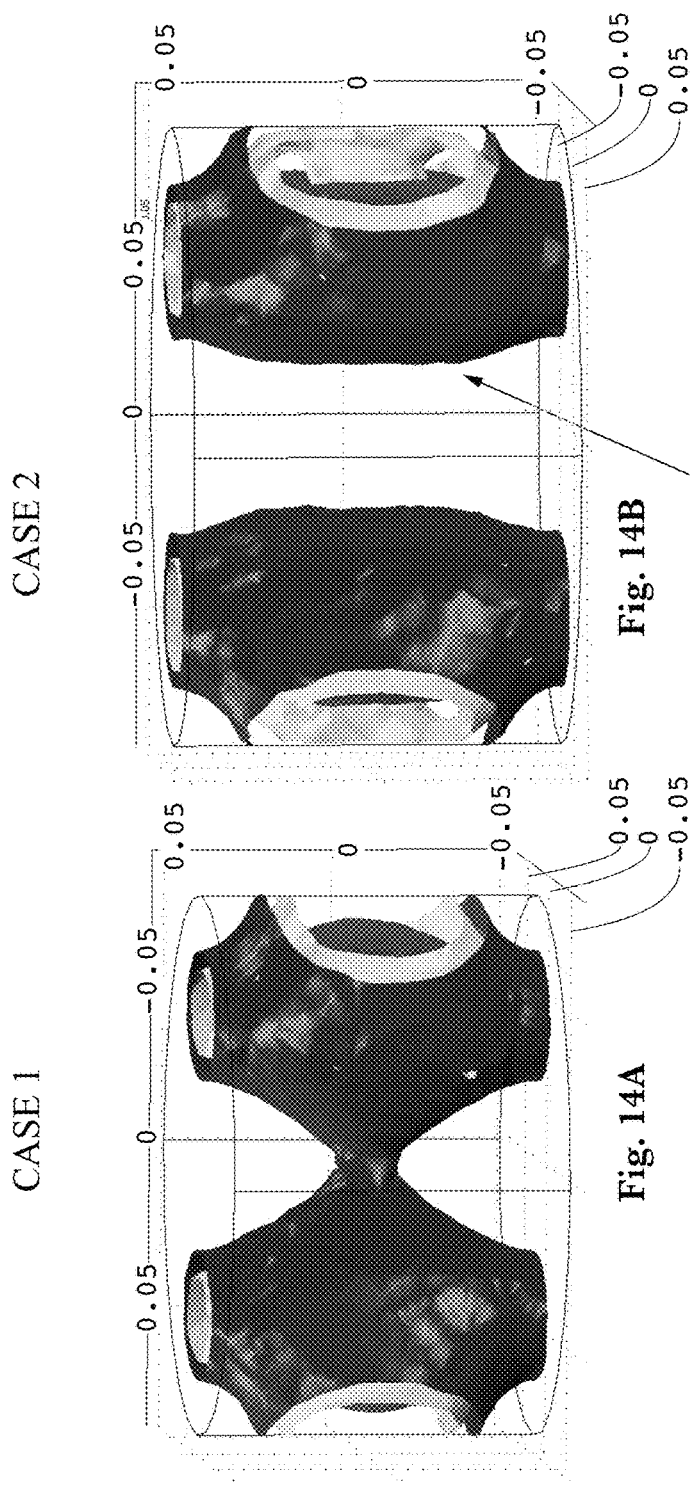

CASES 3&4: ADJACENT PLATES PLACEMENT
CASE 3: Vp1 = Vp2 = Vp3 = Vp4 = +5Volts; Vn1 = Vn2 = Vn3 = Vn4 = -5Volts
CASE 4: Vp1 = +1, Vp2 = +3, Vp3 = +5, Vp4 = +7; Vn1 = -1, Vn2 = -3, Vn3 = -7, Vn4 = -7

ADAPTIVE AND CONVENTIONAL PLATES IN 2D DEPICTION

CONVENTIONAL PLATE

ADAPTIVE PLATE

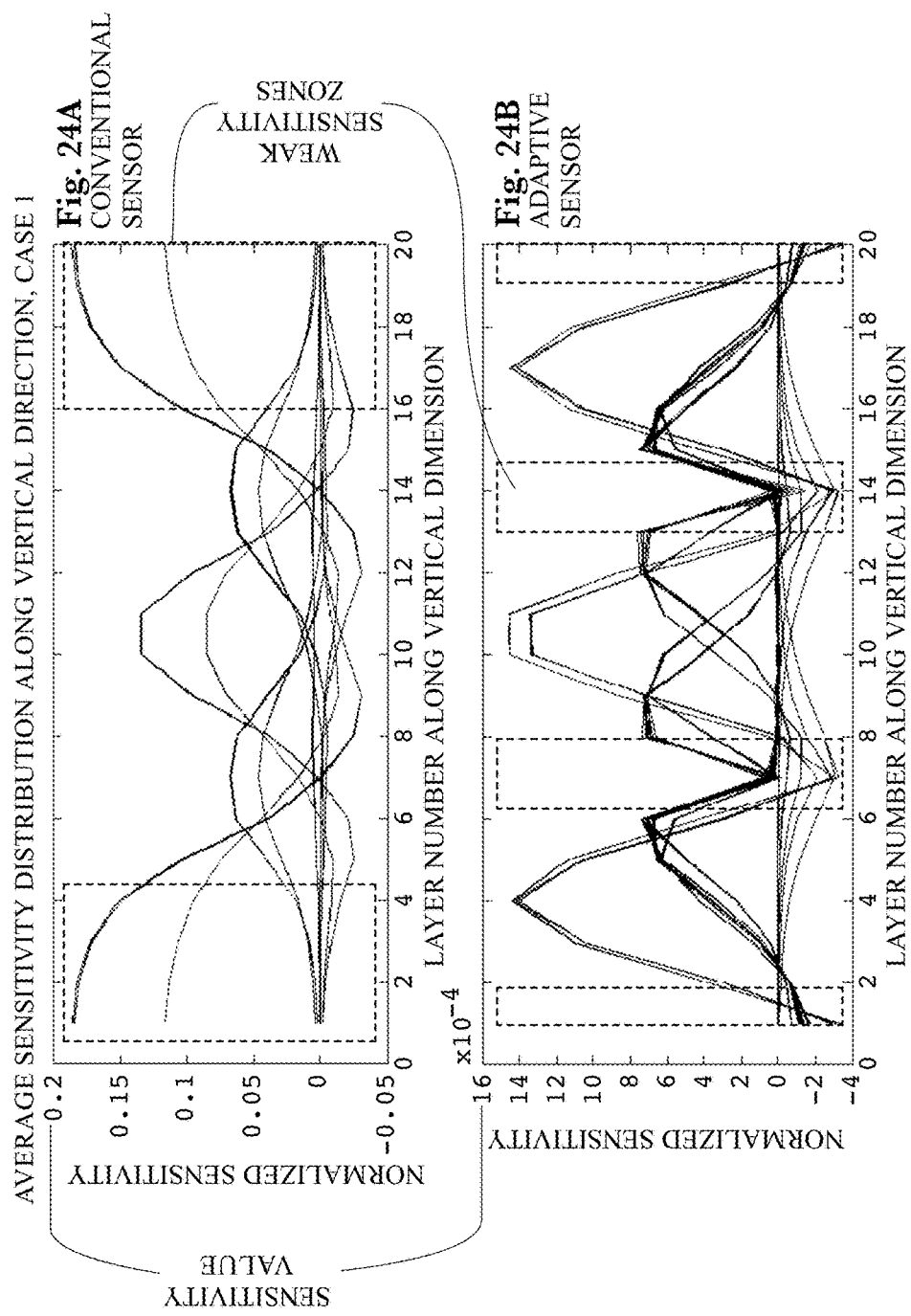

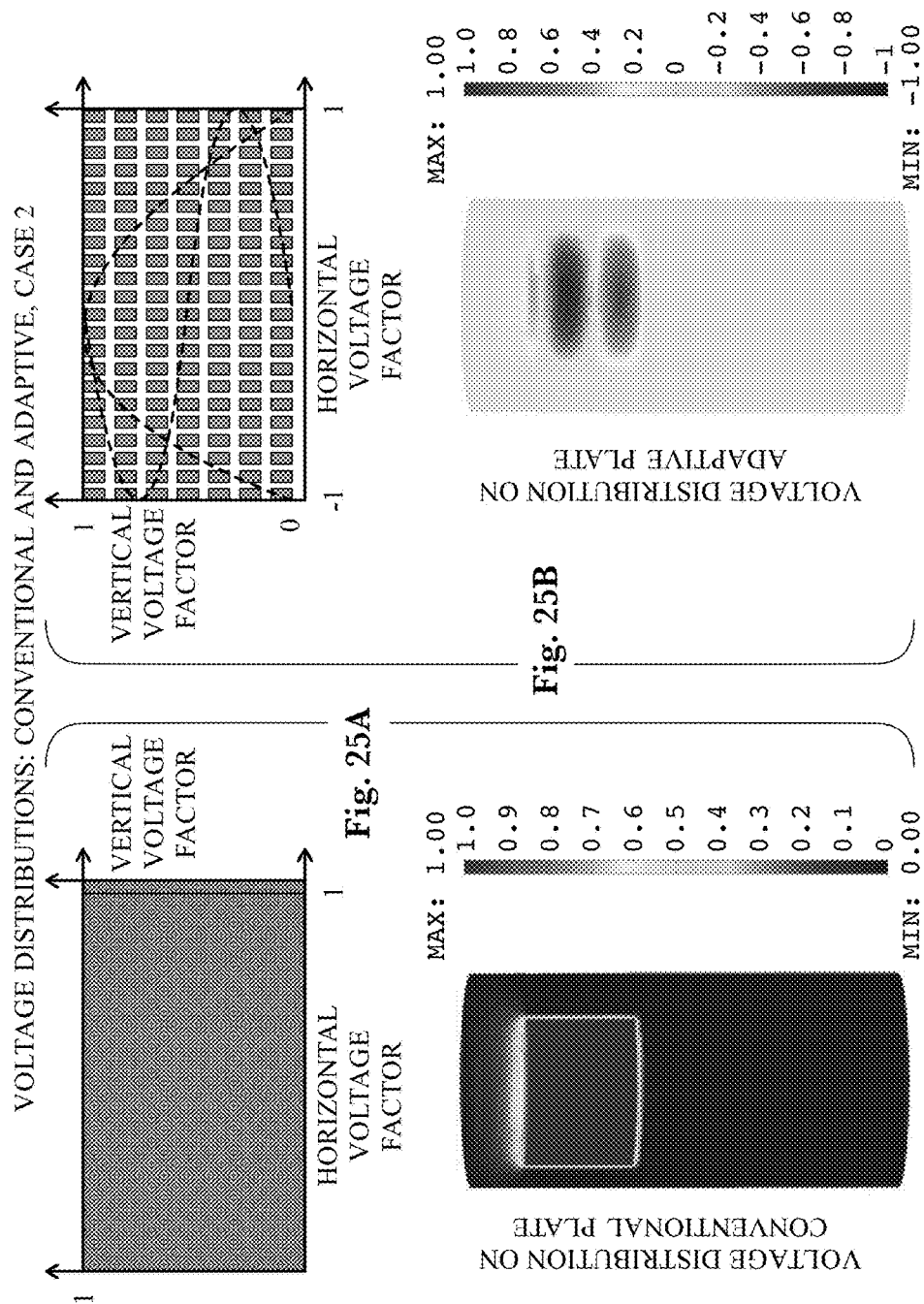

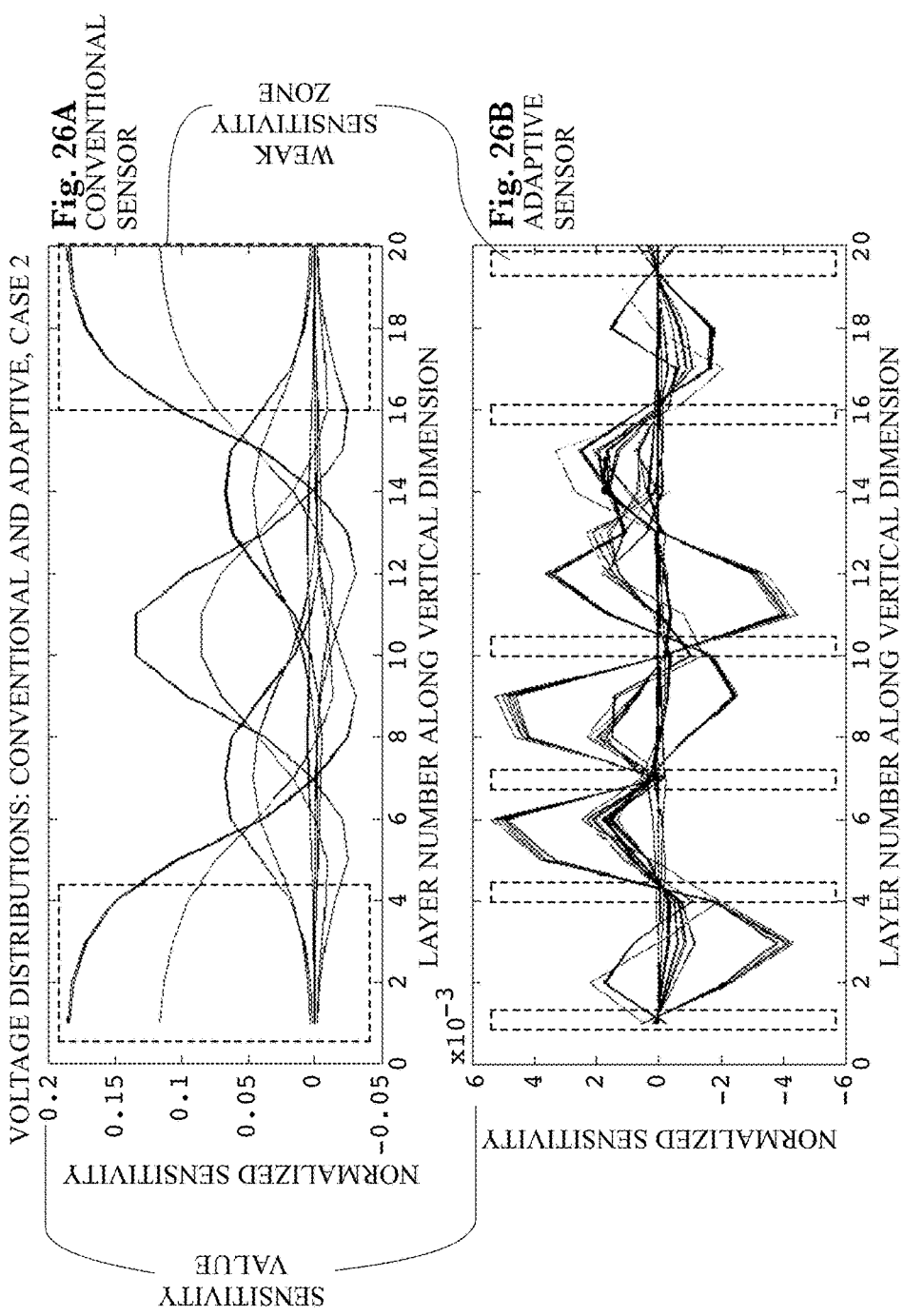

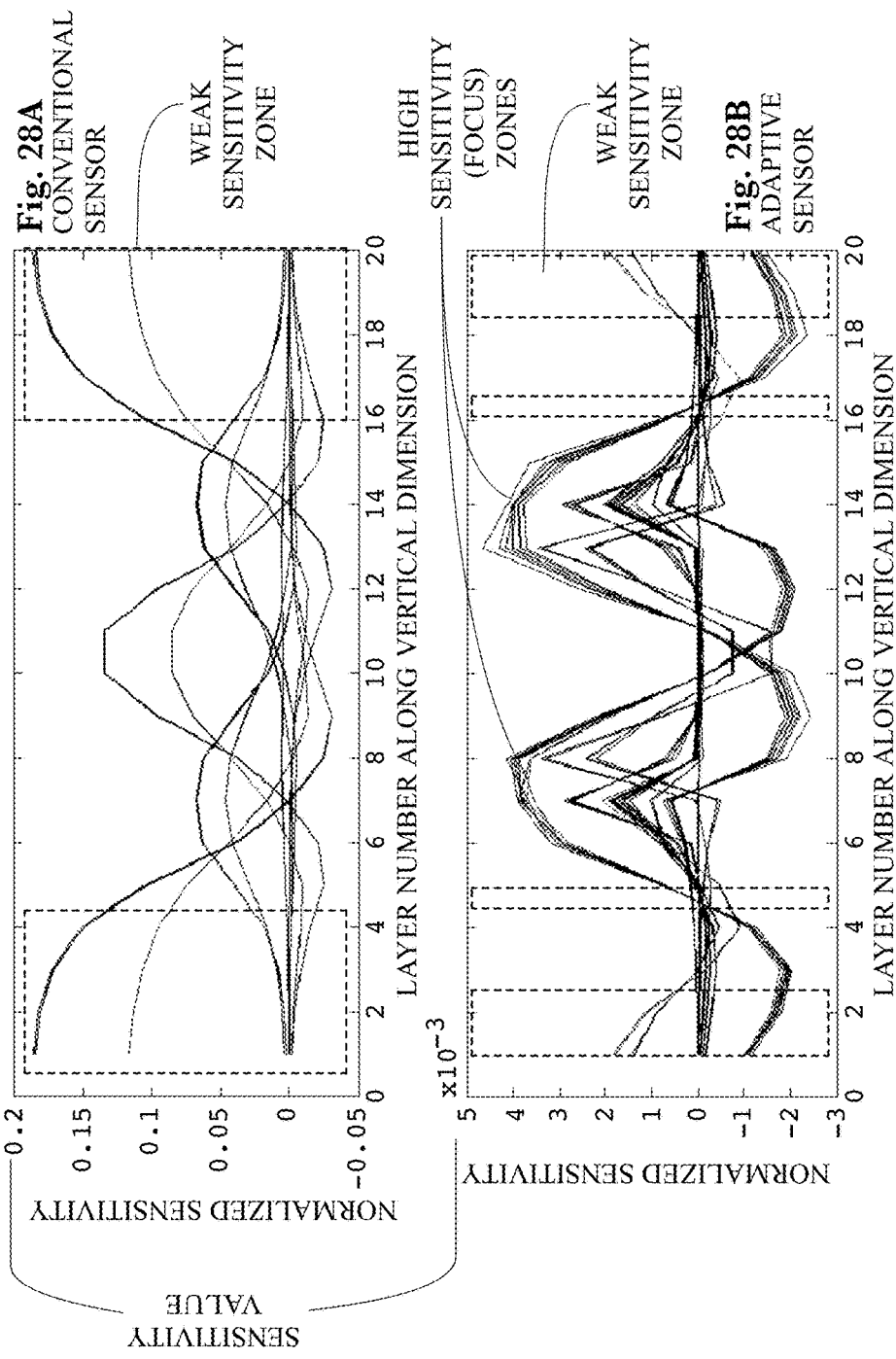

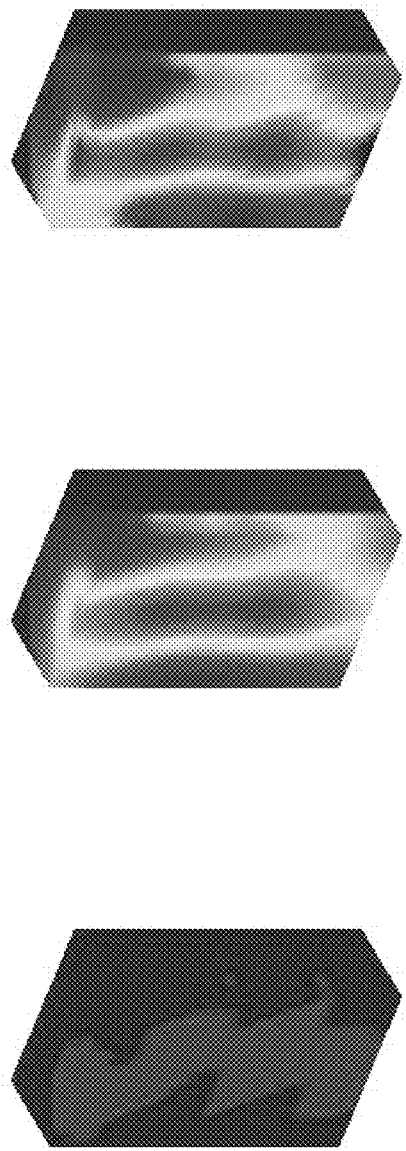
SLICED RECONSTRUCTION RESULTS: HIGHER RESOLUTION
Fig. 31A  Original Distribution
Fig. 31B  Conventional Sensor
Fig. 31C  Adaptive Sensor EXAMPLE: VOLTAGE DISTRIBUTION THROUGH RESISTORS
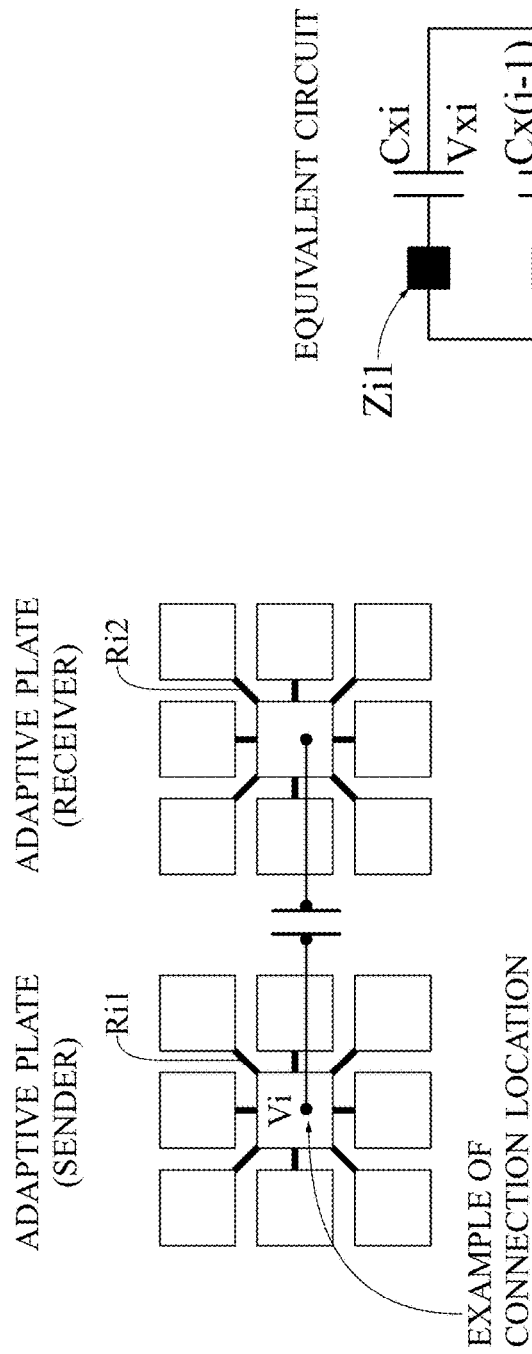
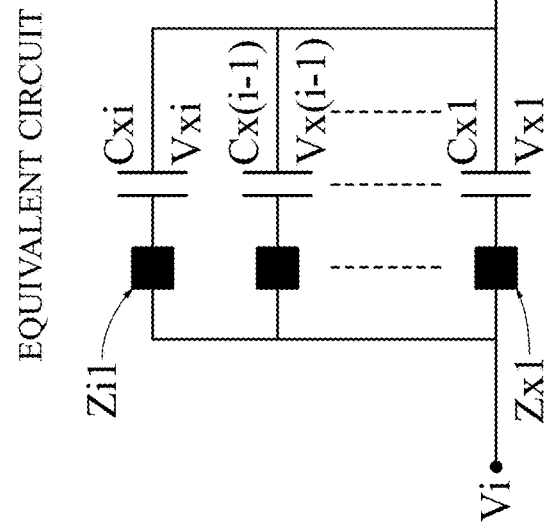
Fig. 34

ADAPTIVE ELECTRICAL CAPACITANCE VOLUME TOMOGRAPHY

CROSS-REFERENCE TO RELATED APPLICATIONS

This patent application is a continuation of U.S. application Ser. No. 13/644,973, filed Oct. 4, 2012, which claims the benefit of U.S. Provisional Patent Application No. 61/543,233, filed Oct. 4, 2011, both of which are hereby incorporated by reference in their entirety as if fully recited herein.

BACKGROUND OF THE INVENTIVE FIELD

The present invention is directed to process tomography and, in particular, to an electrical capacitance volume tomography (ECVT) system and using an adaptive capacitance sensor that allows focusing of the imaging region, increasing of volume image resolution, and steering of the electric field direction toward the region of interest.

Dynamic ECVT is a technology that senses measured capacitances between a sensor region to generate a whole volume image of the region. ECVT technology has been applied in providing imaging of objects moving through a pipe for example. ECVT has provided insights into multiphase flow phenomena in many industrial processes often in a combination of gas, liquid, and solid states, including pneumatic conveying, oil pipe lines, fluidized beds, bubble columns and many other chemical and biochemical processes. It may also be used for imaging biological processes and tissues.

An ECVT system is generally made up of a sensor, sensor electronics and a computer system for reconstruction of the image sensed by the sensor. An ECVT sensor is generally comprised of n electrodes or plates placed around a region of interest, in one embodiment providing $n(n-1)/2$ independent mutual capacitance measurements which are used for image reconstruction. Image reconstruction is performed by collecting capacitance data from the electrodes placed around the wall outside the vessel.

Further details regarding the theory and application of ECVT, sensor design, image reconstruction, and deployment of an ECVT system are found in the U.S. Patent Application Publication No. U.S. 2010/0097374 (U.S. patent application Ser. No. 11/909,548), the relevant disclosures of which are included by reference thereto as if fully set forth herein.

The present invention addresses resolution issues present with traditional ECVT technology. More particularly, the present invention addresses various factors that limit ECVT resolution, including:

The limited number of capacitance plates, and arrangements thereof, that can be used;

Limited sensitivity matrix produced from an uneven distribution of electric field intensity between different plate combinations;

Ill-conditioned system that makes the system more sensitive to noise at sections of the imaging domain compared to others;

Soft field nature of ECVT that is a consequence of the electric field changing its distribution inside the imaging domain based on change of material distribution; and the inability to focus the sensors to a particular region of the imaging domain to allow for more focused reconstructed imaging;

the ill-posed inverse problem inherit in ECVT, which is a result of attempting to reconstruct a number of voxels that is much higher than measured data (i.e., less independent equations with more unknowns);

the limited number of independent capacitance measurements used to reconstruct a volume image;

the minimum required capacitance plate size that restricts scale of region being imaged;

the limited length of capacitance sensor restricted by maximum distance between plates and minimum size of each plate in an ECVT sensor;

the lack of flexibility in applying different voltage signals simultaneously to address different imaging applications.

The present invention is based on an adaptive capacitor sensor array, and associated sensor electronic circuit, that allows focusing of the imaging region and the steering of the electric field direction toward the region of interest. It also allows for higher imaging resolution, increased number of independent capacitance measurements, and relaxation of sensor size limitations.

SUMMARY OF THE GENERAL INVENTIVE CONCEPT

In the preferred embodiment, the ECVT electrodes are comprised of an array of smaller capacitance segments that may be individually addressed. For example, each segment may be activated with different amplitudes, phase shifts, or frequency to provide the desired sensitivity matrix distribution. In one embodiment, the array of selected capacitance segments can form many pairs of capacitance electrodes or plates without reducing overall plate size. The capacitance segments can also be joined in different configurations to provide different designs. The term "envelope" refers to the shape of different voltage amplitudes on segments of one plate. Excitation frequency is the frequency of the signal applied to each segment.

The sensor electronics of the present invention is designed to detect and measure the capacitance for the adaptive ECVT sensor of the present invention. For example, the difference in electrical energy stored in the adaptive ECVT sensor would be measured between an empty state and a state where an object is introduced into the imaging domain (e.g., between the electrodes). In a preferred embodiment of the invention, the term "adaptive" means the ability to provide selective or high resolution control through the application of voltage or voltage distributions to a plate having an array of capacitance segments. The change in overall energy of the system due to the introduction of a dielectric material in the imaging domain is used to calculate the change in capacitance related to the dielectric material. The change in capacitance can be calculated from the change in stored energy. Sensor electronics can also be designed by placing individual segment circuits in parallel yielding a summation of currents representing total capacitance between segments under interrogation. By individually addressing the capacitance segments of the electrodes of the present invention, electric field distribution inside the imaging domain can be controlled to provide the desired sensitivity matrix, focus the electric field, and increase overall resolution of reconstructed images. Voltage distribution can also be achieved by using a conventional measuring circuit with a sensor that distributes voltages through a voltage divider.

Tomography system based on adaptive sensors technology can be used in many different industrial and medical applications. Examples of industries that can utilize developed technology are energy, pharmaceutical, chemical, aerospace, petrochemical, process engineering, healthcare, and multi-phase flow industries. In one example embodiment of the invention, the sensor for use in an electrical capacitance tomography system, is comprised of: a first electrode comprised of a plurality of capacitance segments; a second electrode spaced apart from the first electrode, the second electrode comprised of a plurality of capacitance segments; where the plurality of capacitance segments of the first electrode are individually addressable with voltages; where the capacitance segments of the first electrode form capacitors with corresponding capacitance segments of the second electrode; and where the second electrode is connected to a measuring circuit and wherein the capacitors induce currents in the measuring circuit when charged, the current used to obtain capacitance levels of the capacitors.

The sensor may also be comprised of: a third electrode comprised of a plurality of capacitance segments; a fourth electrode comprised of a plurality of capacitance segments; where the first, second, third and fourth electrodes are placed in a predetermined arrangement with respect to each other wherein the arrangement is adapted to fit around a pipe or tube; where the plurality of capacitance segments of the second, third and fourth electrodes are individually addressable with voltages; where the capacitance segments of each of the first, second, third, and fourth electrodes may be paired with corresponding capacitance segments from the other electrodes to form capacitors; and where the capacitors may be connected to a measuring circuit and wherein the capacitors induce currents in the measuring circuit when charged, the current used to obtain capacitance levels of the capacitors.

An electrical capacitance tomography system for use with the sensor of the present invention is comprised of an image reconstruction processor in communication with the measuring circuit for providing an image of the area between the first, second, third and fourth electrodes based on data collected from the measuring circuit.

In another embodiment, the ECVT system of the present invention may be used in conjunction with humans and animals to detect fluid/object flow and different tissues through the body of humans and animals. In such an embodiment, the sensors of the present invention can be place around a human or animal (fully or partially) to detect fluid/object flow according to the principles of the present invention.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIGS. 12A and 12B illustrate top cross-sectional views of electric field distributions for two example embodiments.

FIGS. 13A and 13B illustrate isosurface views of electric field distributions for two example embodiments at the 50 v/m level.

FIGS. 14A and 14B illustrate isosurface views of electric field distributions for two example embodiments at the 75 v/m level.

FIGS. 24A and 24B illustrate average sensitivity along the vertical direction of a conventional ECVT and adaptive ECVT sensor, respectively, for the example shown in FIGS. 23A and 23B.

FIGS. 25A and 25B illustrate another example of voltage distributions for one plate in a conventional and adaptive ECVT sensor; respectively.

FIGS. 26A and 26B illustrate average sensitivity along the vertical direction of a conventional ECVT and adaptive ECVT sensor, respectively, for the example shown in FIGS. 25A and 25B.

FIGS. 28A and 28B illustrate average sensitivity along the vertical direction of conventional ECVT and adaptive ECVT sensor, respectively, for the example shown in FIGS. 27A and 27B.

FIGS. 31A, 31B and 31C are vertical sliced reconstruction results for simulated capacitance data of an example shape.

FIG. 34 illustrates an example circuit design with its equivalent representation when voltage control is in adaptive sensor side.

DETAILED DESCRIPTION OF EXEMPLARY EMBODIMENT(S)

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

Figure 1:
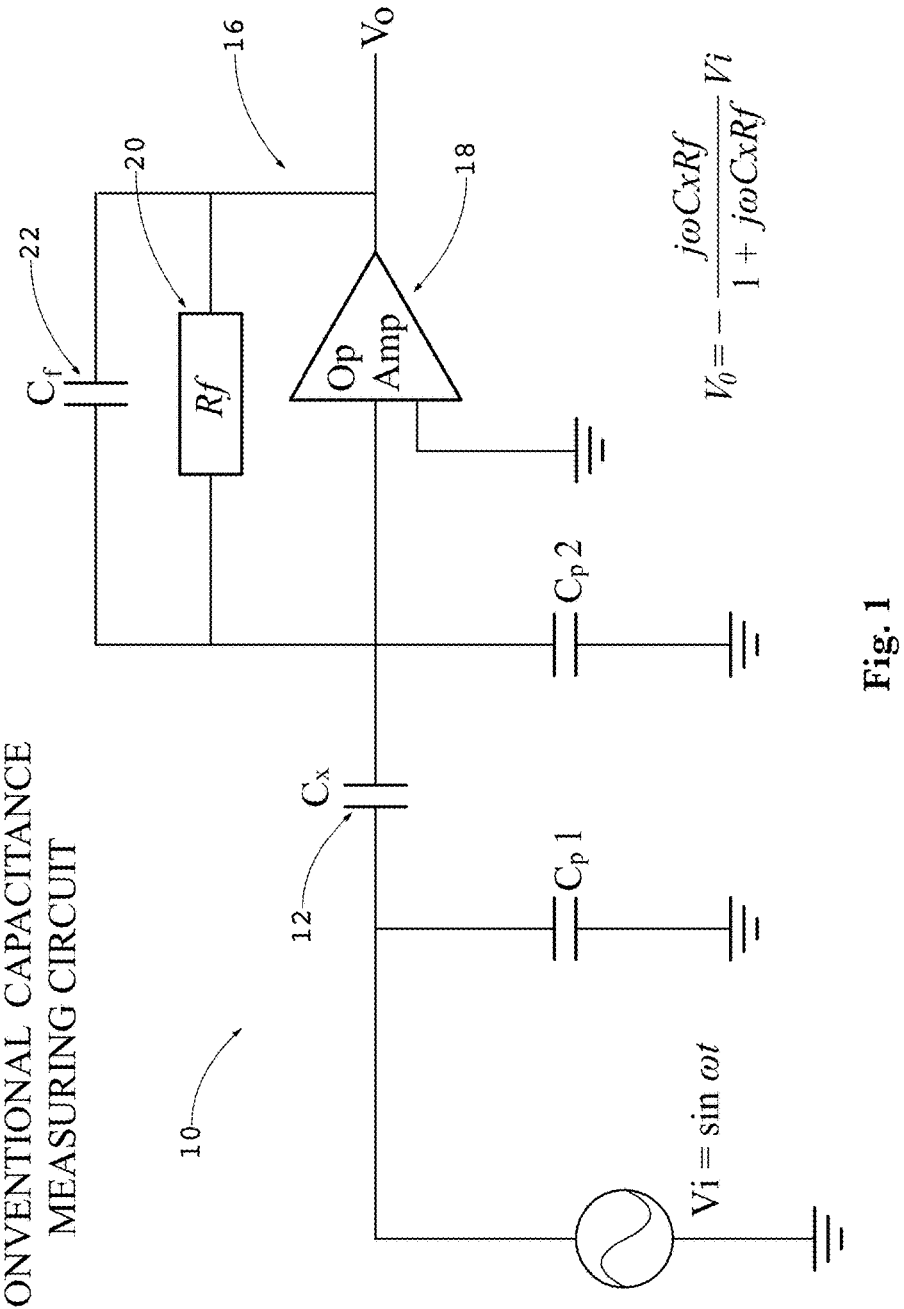
FIG. 1 illustrates one example of a conventional circuit for measuring capacitance.

As depicted in FIGS. 1A and 1B of U.S. Patent Application Publication No. U.S. 2010/0097374 referenced herein, an array of electrodes (e.g., capacitance plates) are arranged to form a capacitance sensor. In one application, this sensor may be placed around a pipe or vent to detect movement within the receptacle to provide imaging data. In a conventional ECVT system, the sensor is made up of capacitance plates where the capacitance is measure between a selected pair of plates. The principle of the basic measuring circuit involves connecting one plate (source electrode or sending electrode) of the sensor to a voltage (e.g., Vi) and another plate (detecting electrode or receiving electrode) to a capacitance measurement circuit. FIG. 1 illustrates one example of a conventional circuit 10 for measuring capacitance. Cx shown at 12 represents the capacitor formed from the selected source and detecting electrode. The portion of the circuit to the right of Cx is the basic capacitance measuring circuit. In one embodiment, the voltage source Vi and capacitance measuring portion of the circuit 16 are connected to the source and detecting electrodes, respectively, using CMOS switches. In a typical operating cycle, the capacitor Cx is charged to voltage Vi and then is discharged which causes current to flow into the capacitance measurement portion of the circuit. At least a portion of the current generated flows through the operational amplifier 18. The output voltage Vo is related to the value of the resistor Rf 20 and capacitor Cf 22 (see formula referenced in FIG. 1). In one embodiment, the capacitance is measured between all of the plates (selecting two plates at a time) of the sensor array and the data collected is used to reproduce an image of the multiphase flow between the sensors.

Figure 2:
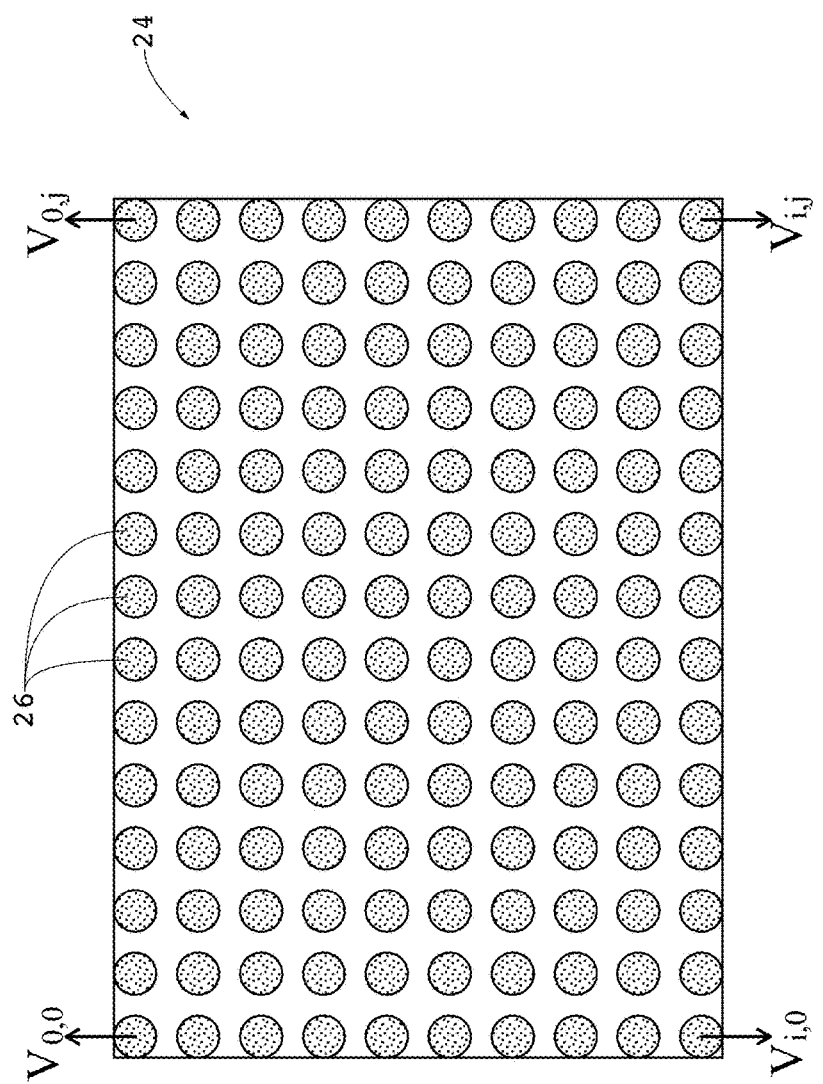
FIG. 2 illustrates one example of an adaptive capacitance plate (electrode) of the present invention.

FIG. 2 illustrates one example of an adaptive capacitance plate (electrode) 24 of the present invention. In this example, the electrodes of the sensor array are comprised of a plurality of smaller plates or segments 26 (e.g., smaller capacitance plates or electrodes) which can be individually addressed. The shape of the capacitance segments can be made up various shapes where each plate can be activated with the same or different voltages, frequencies, or phase shifts. Segments of each electrode are preferably connected together in parallel, with voltage control applied independently to each segment. Segments of interest chosen to form sender or receiver plates can be activated by electronic switches that open or close to connect a particular segment in parallel with others chosen in same plate.

In a conventional ECVT sensor, each plate is activated by equal voltage distribution or a voltage distribution "envelope." In a preferred embodiment, "envelope" means the shape of the voltage distribution applied to the plate or capacitance segments. Changing of the envelope applied to the capacitance segments of a plate allows control over sensor sensitivity and allows focusing of the sensor. Some of the ways to change the envelope is to change the frequency of the applied voltage, change the voltage applied, or change the phase of the frequency applied. The following description will demonstrate example applications and features of an adaptive ECVT by applying different envelopes on each plate. This is preferably achieved by dividing each plate into small segments and distributing voltage according the envelope. These examples demonstrate how to focus and provide 3D sensitivity of each adaptive ECVT sensor with different envelopes. In one embodiment, focus may be achieved by changing envelope frequency. In one embodiment of the invention, change of envelope phase shift changes sensitivity distribution.

Figure 3A:
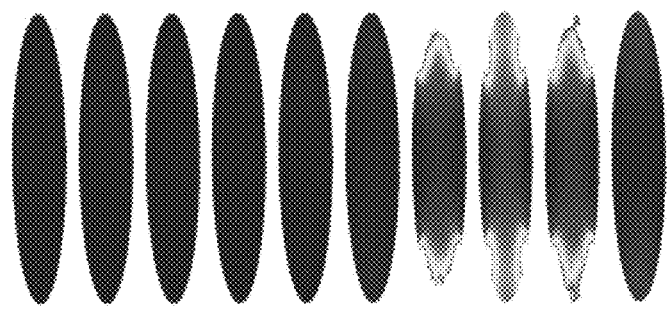
FIGS. 3A and 3B illustrate example electric field distributions for opposite plates of a traditional ECVT sensor.
Figure 3B:
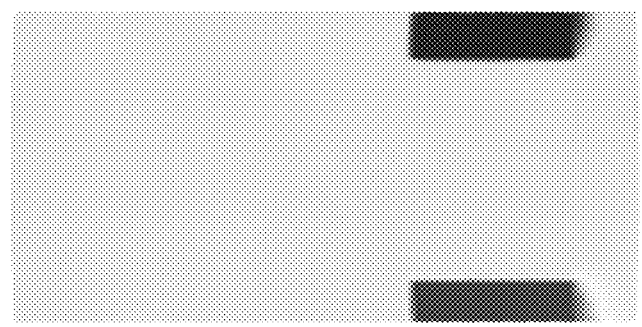

FIGS. 3A and 3B illustrate example electric field distributions for opposite plates of a traditional ECVT sensor. As illustrated, the electric field is generally stronger at the edges and weaker toward the center. The sensitivity matrix from such a distribution is generally ill-conditioned.

Figure 4B:
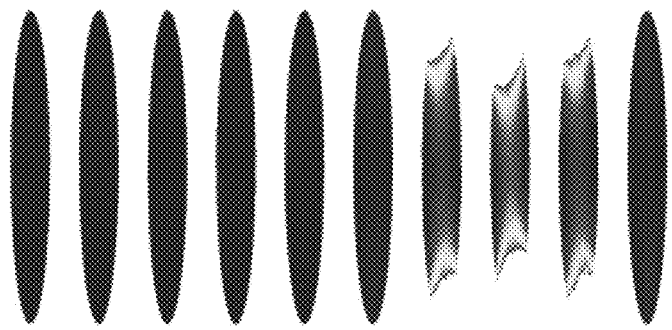
FIGS. 4A and 4B illustrate example electric field distributions for opposite plates of an adaptive ECVT sensor.
Figure 4A:
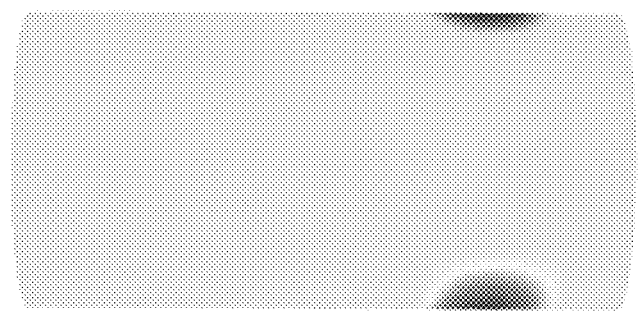

FIGS. 4A and 4B illustrate example electric field distributions for opposite plates of an adaptive ECVT sensor. In the preferred embodiment, the voltage on the plates follows a 2D sine function. As illustrated, the electric field is generally stronger towards the center and more uniform throughout the imaging area.

Figure 5A:
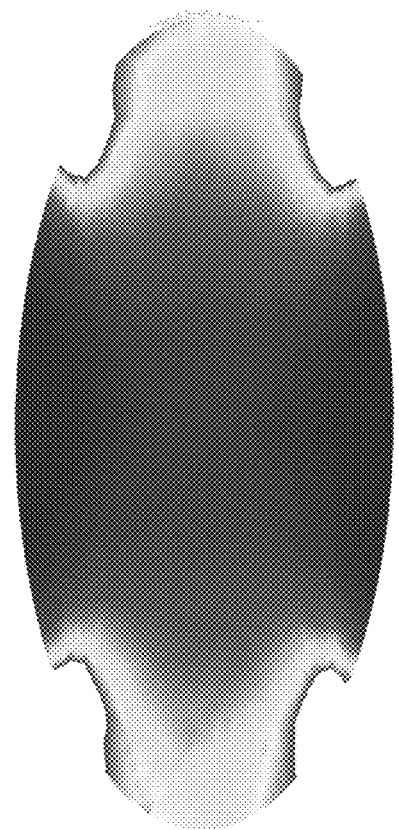
FIGS. 5A and 5B illustrate cross-sectional views of electric field distribution for traditional and adaptive sensor, respectively.
Figure 5B:

FIGS. 5A and 5B illustrate example cross-sectional views of electric field distribution for traditional and adaptive sensors, respectively. In this example, the adaptive sensor is used with a 2D sine distribution with the same amplitude as the traditional sensor of FIG. 5A. The more uniform distribution of electric field of the adaptive sensor will provide higher image resolution.

Figure 22B:
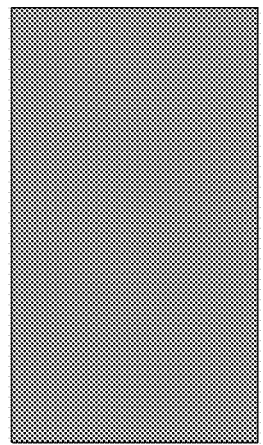
FIGS. 22A, 22B and 22C illustrate an example of using adaptive plates for a conventional ECVT sensor.
Figure 22C:
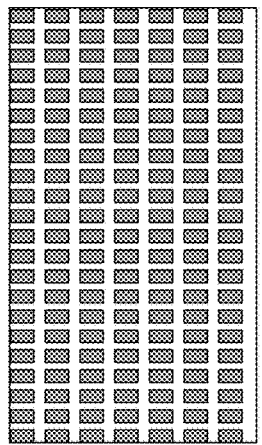
Figure 22A:
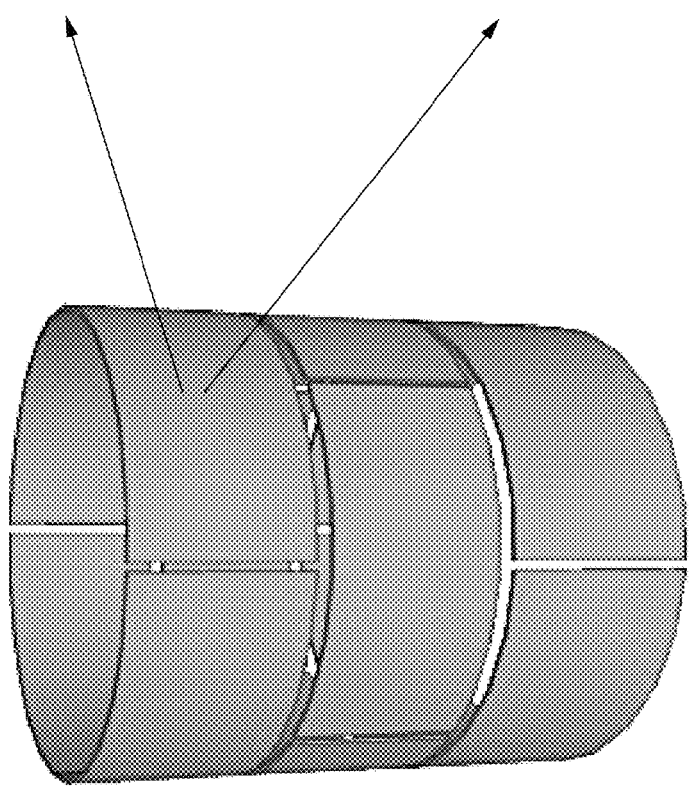

FIGS. 22A, 22B and 22C provide an example of using adaptive plates instead of a conventional ECVT sensor. The adaptive sensor of the present invention is preferably comprised of smaller segments that allows focusing of the sensor. The following figures provide voltage and sensitivity distributions for various examples.

Figures 23A, 23B:
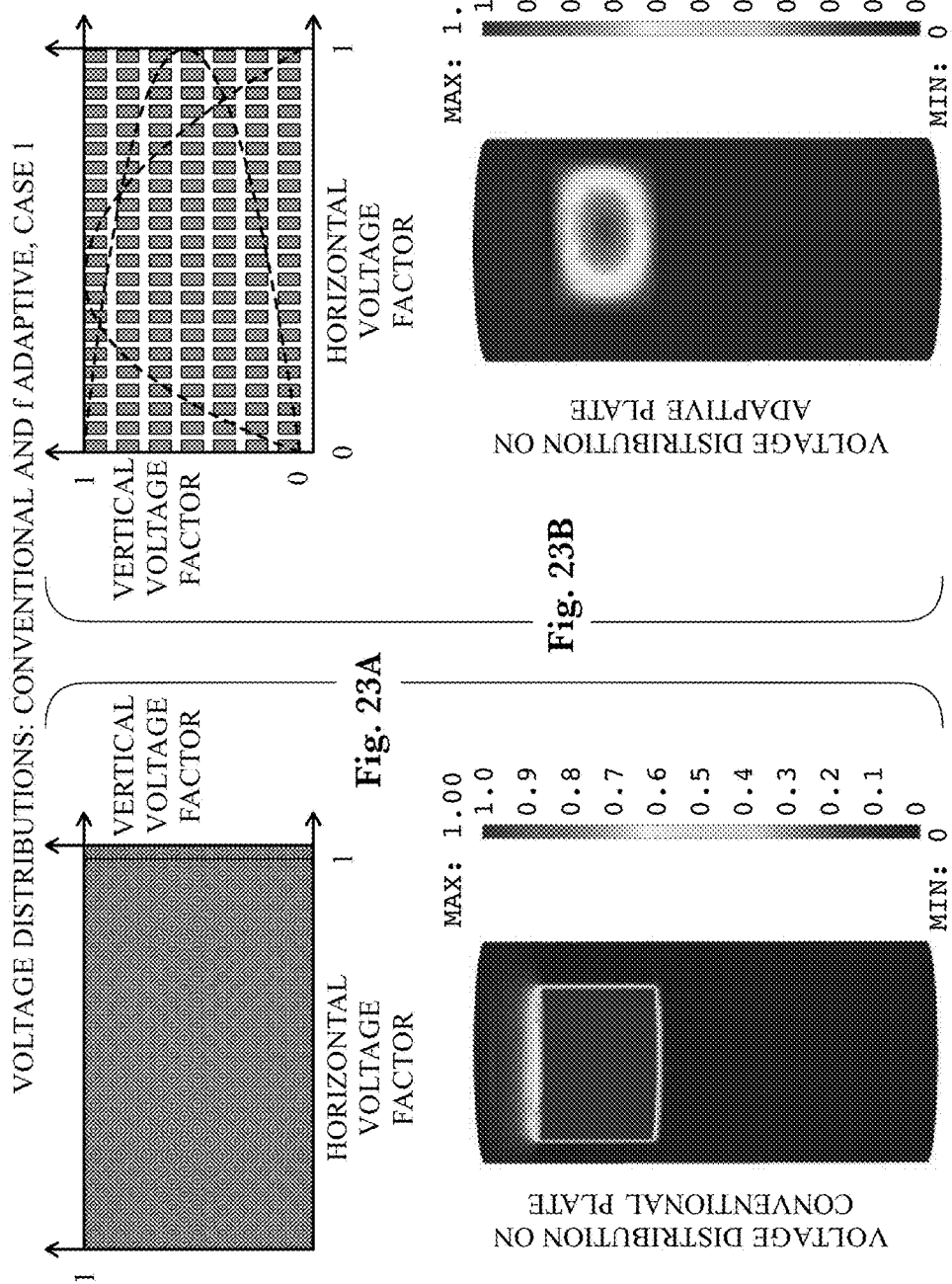
FIGS. 23A and 23B illustrate example voltage distributions for one plate in a conventional and adaptive ECVT sensor, respectively.

FIGS. 23A and 23B illustrate examples of voltage distributions for one plate of a conventional ECVT sensor and an adaptive ECVT sensor, respectively. In this example, voltage is applied on the adaptive plates in a shape of half cycle cosine wave along the vertical and horizontal direction. The period of each cosine is set based on the vertical and horizontal dimension of each plate, respectively. This shape of voltage distribution on each plate is referred to as the "envelope."

FIGS. 24A and 24B illustrate average sensitivity along the vertical direction of conventional ECVT and adaptive ECVT sensors, respectively, for the example of FIG. 23. The adaptive sensor here has a voltage distribution as in FIG. 23B. Weak sensitivity zones, where slope or amplitude are near zero, are highlighted.

FIGS. 25A and 25B illustrate example voltage distributions for one plate in a conventional and adaptive ECVT sensor, respectively. In this example, voltage is applied on the adaptive plates in a shape of a full cycle cosine wave along the vertical and half cosine cycle along the horizontal direction. The period of each cosine is set based on the vertical and horizontal dimension of each plate, respectively.

FIGS. 26A and 26B illustrate example average sensitivity along the vertical direction of a conventional ECVT and adaptive ECVT sensor, respectively, for the example of FIGS. 25A and 25B. The adaptive sensor here has voltage distribution as in FIG. 25B. Weak sensitivity zones, where slope or amplitude is near zero, are highlighted. It is illustrated here, by comparison with FIG. 24, that a change in envelope frequency results in an increase in the number of high and low sensitivity zones. This is referred to as focus of adaptive sensor sensitivity or "beams".

Figures 27A, 27B:
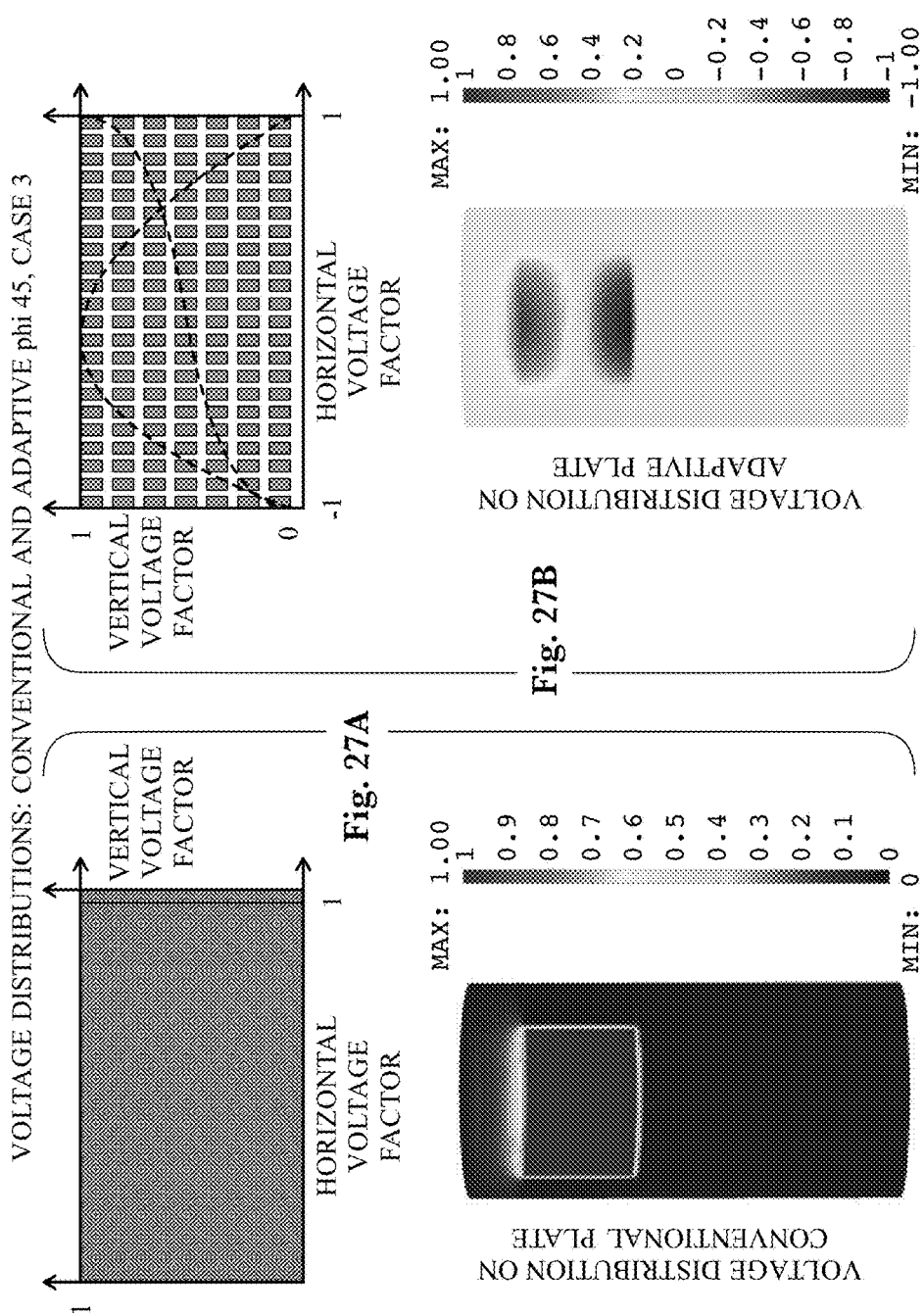
FIGS. 27A and 27B illustrate another example of voltage distributions for one plate in a conventional and adaptive ECVT sensor, respectively.

FIGS. 27A and 27B illustrate example voltage distributions for one plate in a conventional and adaptive ECVT sensor, respectively. In this example, voltage is applied on the adaptive plates in a shape of half cycle cosine wave along the vertical and horizontal direction, respectively, with a 45 degrees phase shift along the vertical direction. The period of each cosine is set based on the vertical and horizontal dimension of each plate, respectively.

FIGS. 28A and 28B illustrate average sensitivity along the vertical direction of a conventional ECVT and adaptive ECVT sensor, respectively, for the example of FIG. 27. The adaptive sensor here has voltage distribution as in FIG. 27B, Weak sensitivity zones, where slope or amplitude are near zero, and strong sensitivity zones, where slope and amplitude are high, are also highlighted. It is illustrated here, by comparison with FIG. 24, that a change in envelope phase results in a change in the location of strong and weak sensitivity locations. This is referred to as steering of adaptive sensor sensitivity or "beams".

Figures 29A, 29B, 29C:
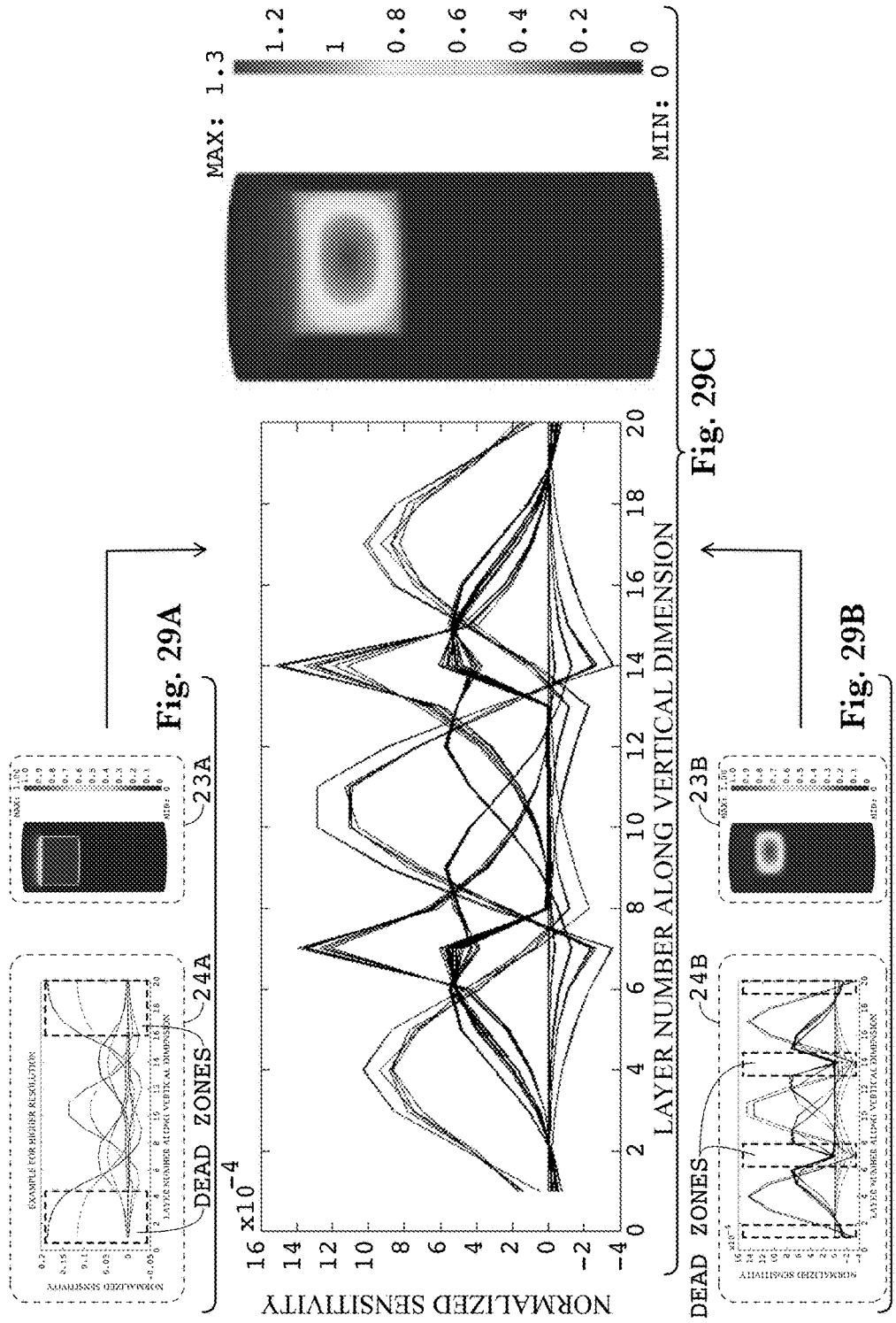
FIGS. 29A, 29B and 29C illustrate the feasibility of combining different voltage distributions to provide desired focus and steering for higher image resolution.

FIGS. 29A, 29B and 29 are examples that illustrate the feasibility of combining different voltage distributions to provide desired focus and steering for higher image resolution. Average sensitivity along the vertical direction of an adaptive ECVT sensor with a combined envelope is depicted in FIG. 29C. Here, through a combined envelope voltage distribution, weak sensitivity zones are eliminated and average sensitivity is leveled over sensor length.

Figures 30A, 30B, 30C:
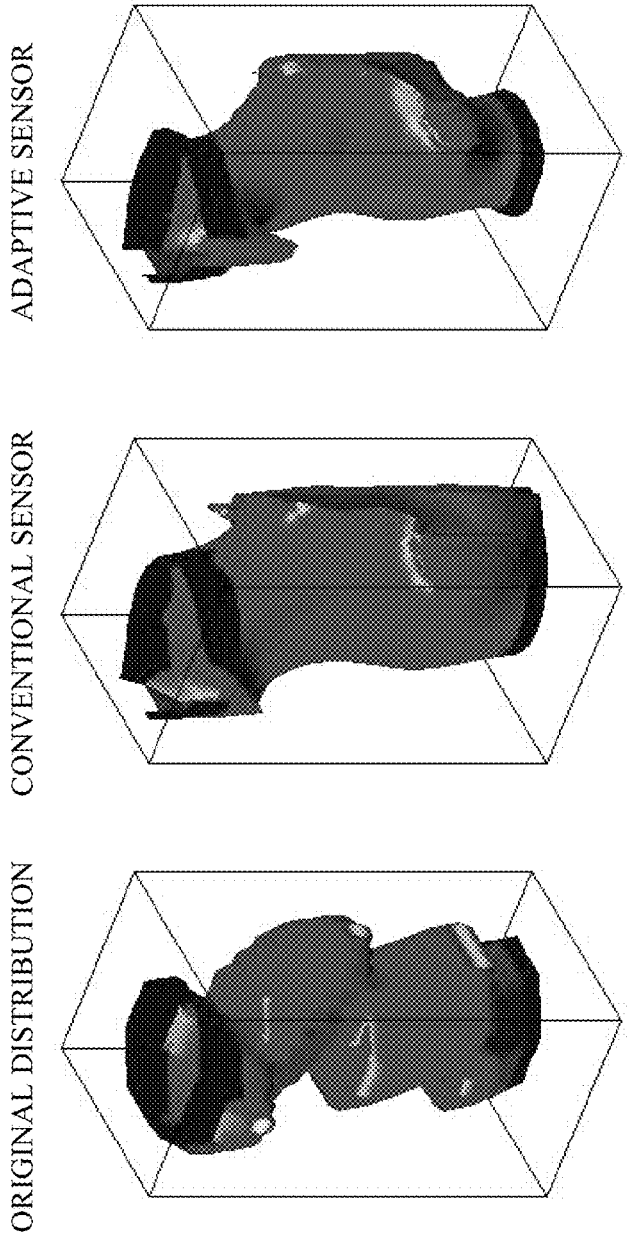
FIGS. 30A, 30B and 30C are isosurface reconstruction results for simulated capacitance data of an example shape.

FIGS. 30B and 30C are example isosurface reconstruction results for simulated capacitance data of the shape in FIG. 30A Capacitance data was simulated using a conventional ECVT sensor and an adaptive ECVT sensor with an envelope as in FIG. 29C. In this example, conventional and adaptive sensors have the same number of plates—twelve. Using adaptive sensors, reconstruction results illustrate better features to the conventional sensor when compared to the original distribution.

FIGS. 31A, 31B and 31C are vertically sliced reconstruction results for simulated capacitance data of the shape in FIG. 30A. Capacitance data was simulated using a conventional ECVT sensor and an adaptive ECVT sensor with an envelope as in FIG. 29C. In this example, conventional and adaptive sensors have the same number of plates—twelve. Using adaptive sensors, reconstruction results illustrate better features to conventional sensor when compared to the original distribution.

Figure 6:
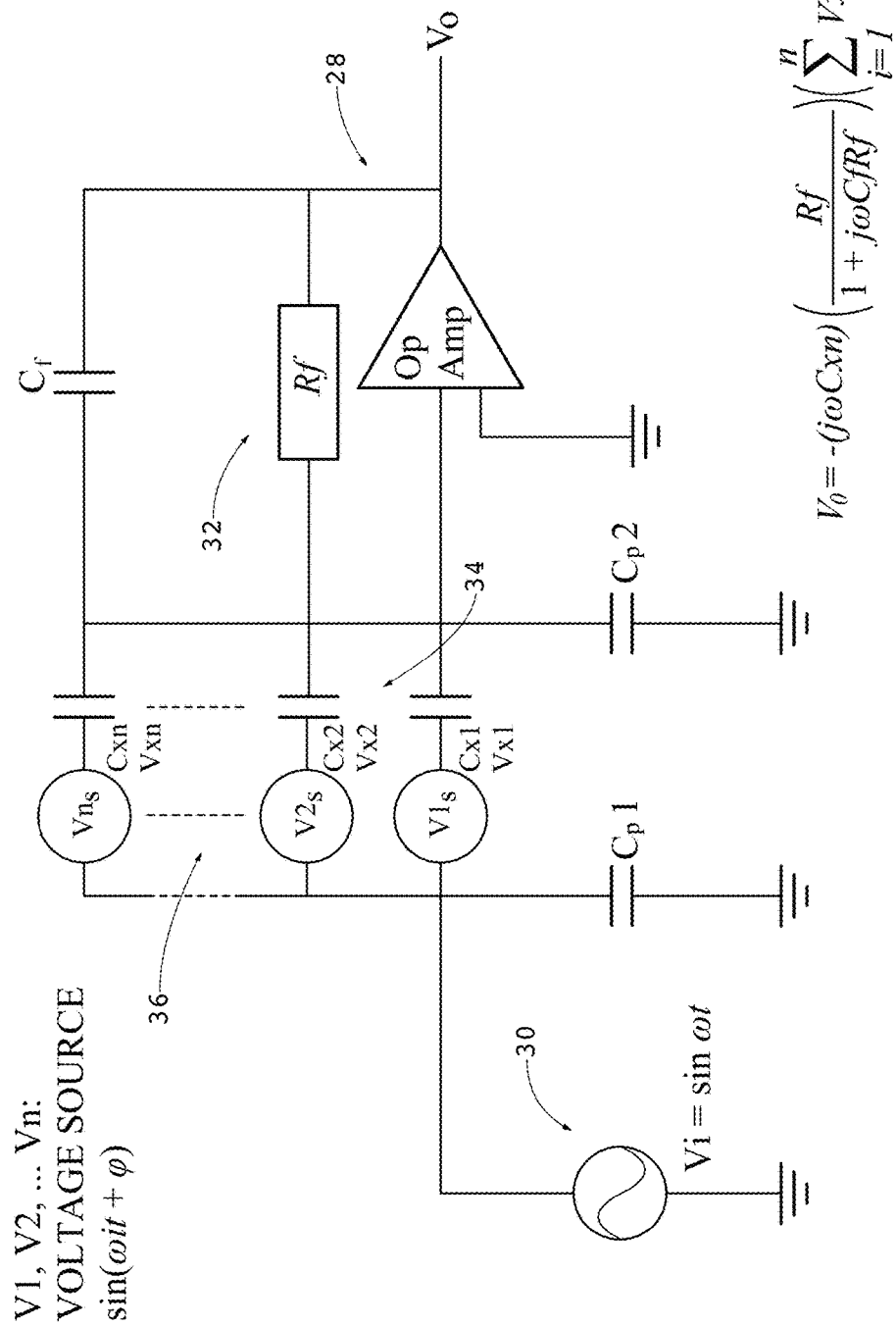
FIG. 6 illustrates one example embodiment of a capacitance measuring circuit for the adaptive sensors of the present invention.

FIG. 6 illustrates one example embodiment of a capacitance measuring circuit 28 for an adaptive sensor of the present invention. Again, a voltage source Vi 30 is connected to an electrode (source or sending electrode) of the adaptive sensor of the present invention. In this embodiment, a capacitance measurement circuit, shown generally at 32, is connected to another electrode (detecting or receiving electrode) of the adaptive sensor so that a capacitance measurement can be obtained for the selected source and detecting electrodes. The capacitors Cx1-Cxn, shown generally at 34, represent the n number of capacitance segments of the selected source electrode and the detecting electrode. As illustrated, each capacitance segment of the electrodes can be individually addressed by separated voltage sources shown generally at 36 (V1-Vn). These voltage sources are used for regulating the voltage levels and phase shifts on the capacitance segments of each of the electrodes on the adaptive sensor. The voltage across each of the capacitor segments (Vxn) is the combination of the voltage source Vi and the voltage sources connected to each capacitor segment (Vn). Accordingly, using the associated formula as depicted in FIG. 6, the measured Vo can be used to calculate each of the equivalent capacitance (Cxn) of the capacitance segments of the activated electrode. The associated formula is for Cxn=Cx1=Cx2 . . . =Cxi. For segments with different capacitance values, the equivalent capacitance is calculated using the formula:

$$V_0 = \left(\frac{j\omega R_f}{1+j\omega C_f R_f}\right)\left(\sum_{i=1}^{n} V_{xi} C_{xi}\right)$$

As discussed, in one embodiment, n(n−1)/2 independent mutual capacitance measurements are measured and used for image reconstruction. For example, the capacitance between each of the electrodes of the sensor are measured in turn and image reconstruction is performed using this capacitance data. In other words, capacitance measurements are obtained from every pair or electrode combination of the sensor, in turn, to be used in image reconstruction.

Different amplitudes of voltage can be applied to different capacitance segments depending on the application and the result desired. For example, the greater amplitudes can be applied to the capacitance segments in the center of the electrodes if it is desired to have more resolution toward the center of the imaging region. Accordingly, interaction between different activated segments, activated with different amplitudes, would change electric field distribution inside the imaging domain, providing control over sensor sensitivity. Control of the electric field distribution would also enable the focusing and zooming of sensor sensitivity to specific imaging regions.

It is appreciated that the voltage sources herein discussed may be connected to the capacitance segments of each of the electrodes of the sensor array using known switch technologies. Using switches, the system can selectively choose which electrodes to activate by connecting the voltage sources to the selected electrodes through the switches. In another embodiment, switching or multiplexing circuit elements can be used to connect the appropriate voltage sources to each of the capacitance segments of the selected electrode allowing various elements to be selectively connected to each capacitance segment depending on the focus and sensitivity desired. For example, voltage sources of greater amplitude may be switched or connected to the capacitance segments in the center of the electrode or imaging domain so as to focus the measurements towards the center of the electrode or imaging domain.

In an alternate embodiment, instead of using different amplitudes, different frequencies may be used to activate electrode segments enabling concurrent measurements of different capacitance values introduced by electric field beams of different frequencies. In yet another alternate embodiment, different phase shifts may be used to activate electrode segments enabling steering of the electric field inside the imaging domain.

In the preferred embodiment, adaptive ECVT technology of the present invention enables increasing capacitance measurements without reducing signal to noise ratio. Adaptive ECVT technology allows a large number of capacitance measurements by connecting different segments together and activating them with different voltage levels. This allows more capacitance measurement without decreasing noise level (e.g., signal integrity is preserved). This allows enhanced image quality.

Figure 7:
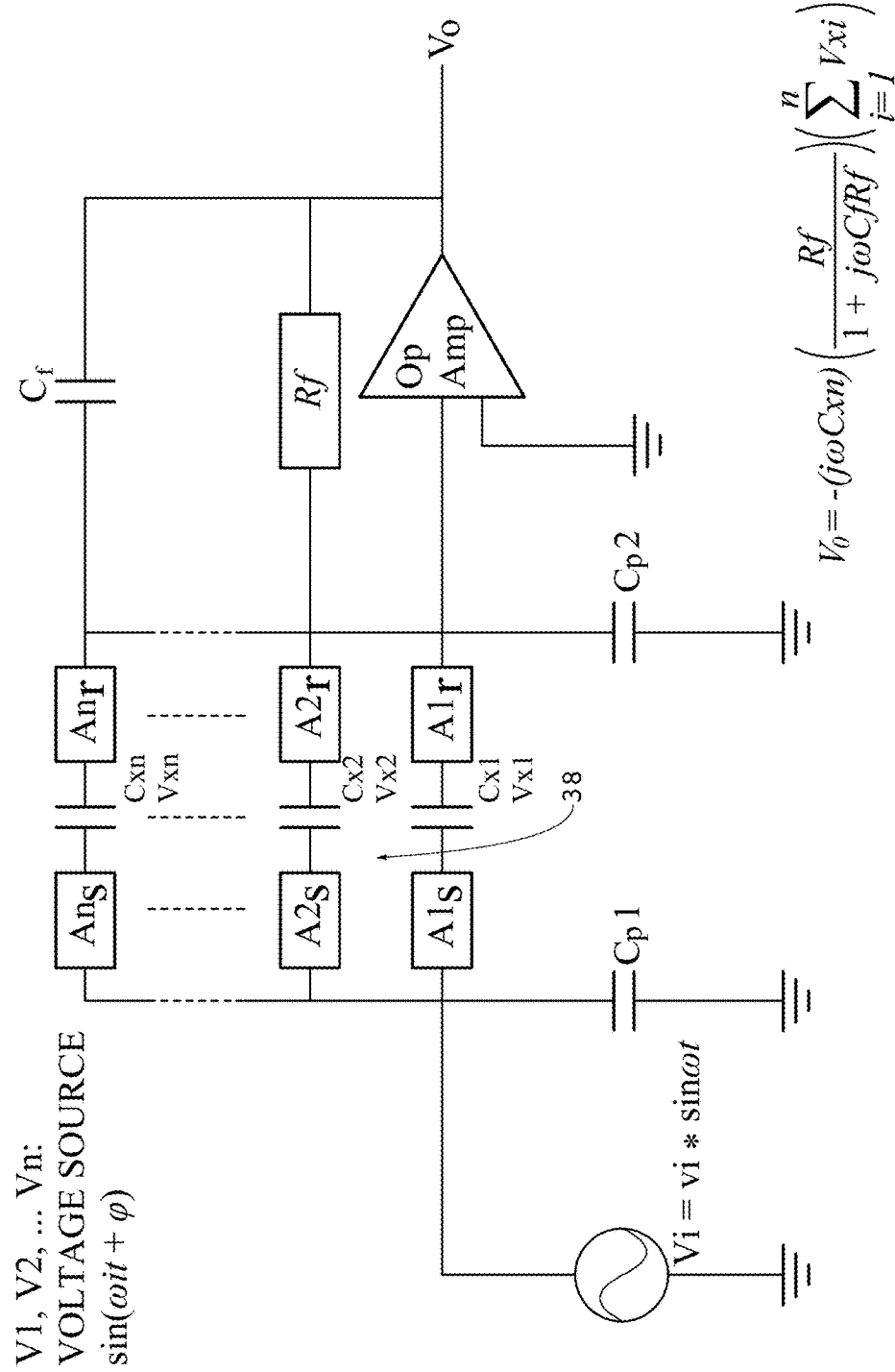
FIG. 7 illustrates another example embodiment of a capacitance measuring circuit for the adaptive sensors of the present invention.
Figure 20:
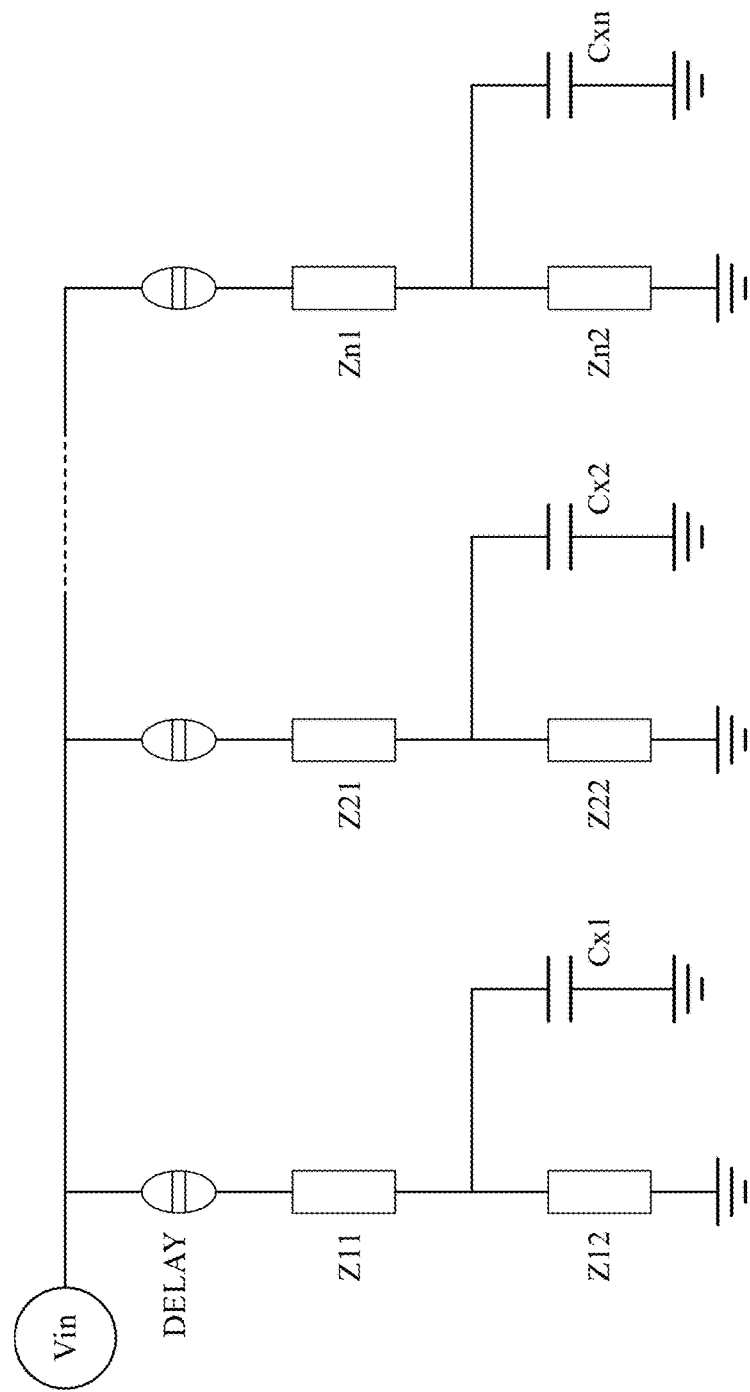
FIG. 20 illustrates an example embodiment of capacitance plates activated by different voltage levels through voltage dividers.

FIG. 7 illustrates another example embodiment of a capacitance measuring circuit for the adaptive sensors of the present invention. In this embodiment, other circuit elements shown as A1-An generally at 38, such as current sources or even passive elements such as resistors, inductors, or capacitors, can be used to regulate the voltages on capacitors Cx1-Cxn. For example, a voltage divider as shown in FIG. 20 can be used to regulate voltages on the individual capacitance segments.

Figure 8:
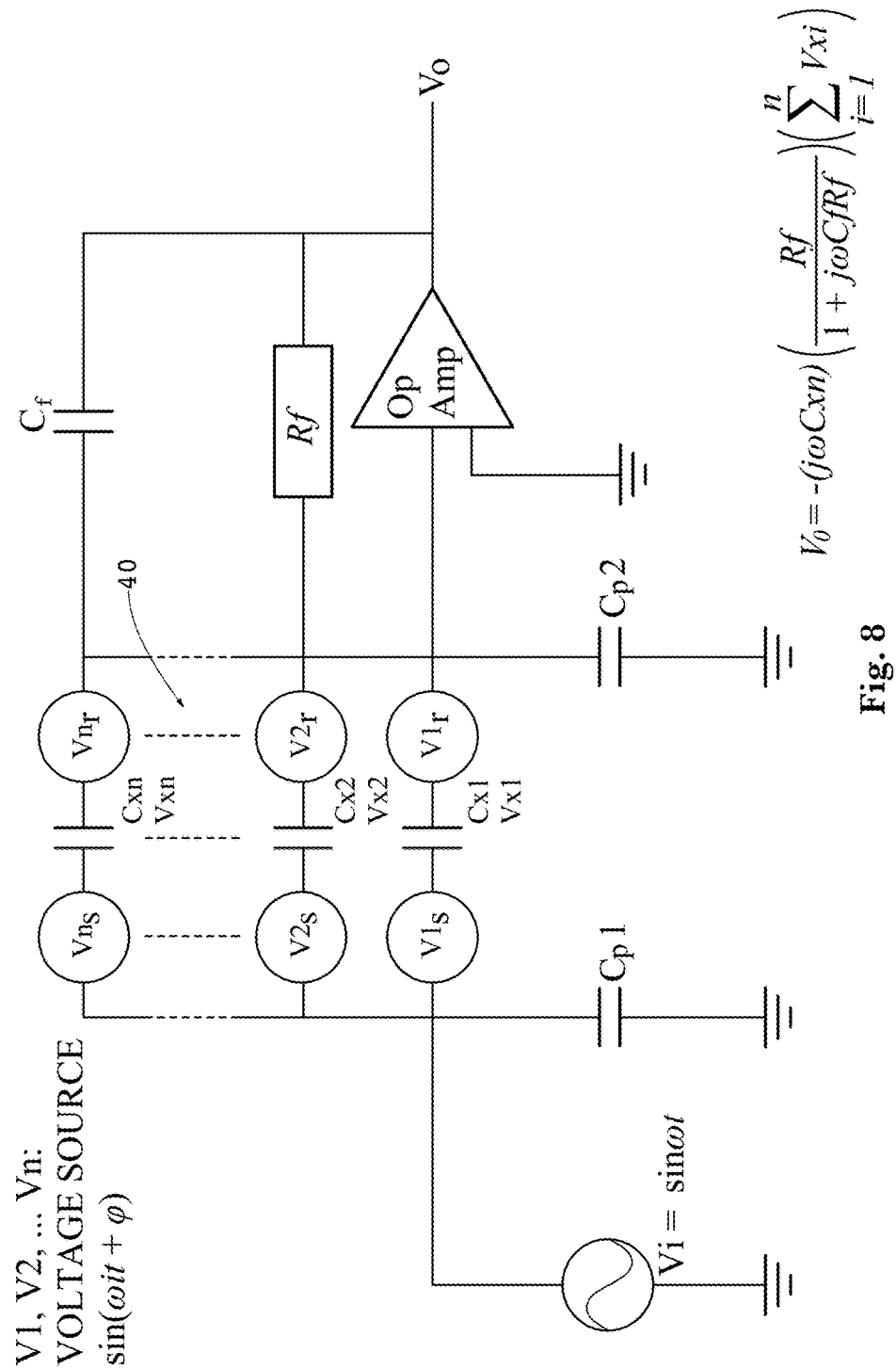
FIG. 8 illustrates another example embodiment of a capacitance measuring circuit for the adaptive sensors of the present invention.

FIG. 8 illustrates another example embodiment of a capacitance measuring circuit for the adaptive sensors of the present invention where voltage sources, shown as V1r-Vnr generally at 40, are also applied to each of the capacitance segments on the detecting electrode side of the sensor to individually address the segments.

Figure 9:
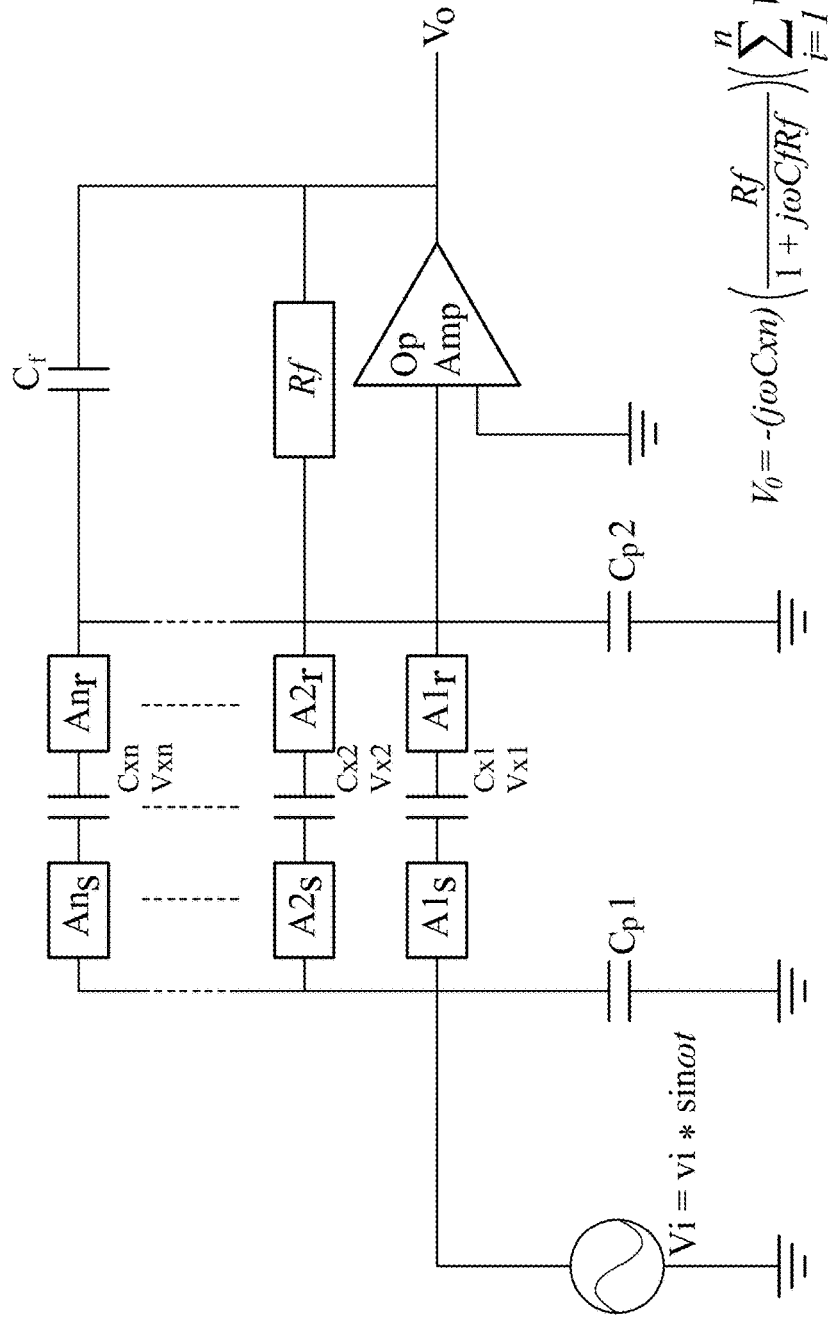
FIG. 9 illustrates another example embodiment of a capacitance measuring circuit for the adaptive sensors of the present invention.

FIG. 9 illustrates another example embodiment of a capacitance measuring circuit for the adaptive sensors of the present invention where other active or passive circuit elements, shown as A1r-Anr, generally at 42, are also applied to each of the capacitance segments on the detecting electrode side of the sensor to individually address the segments.

Figure 10:
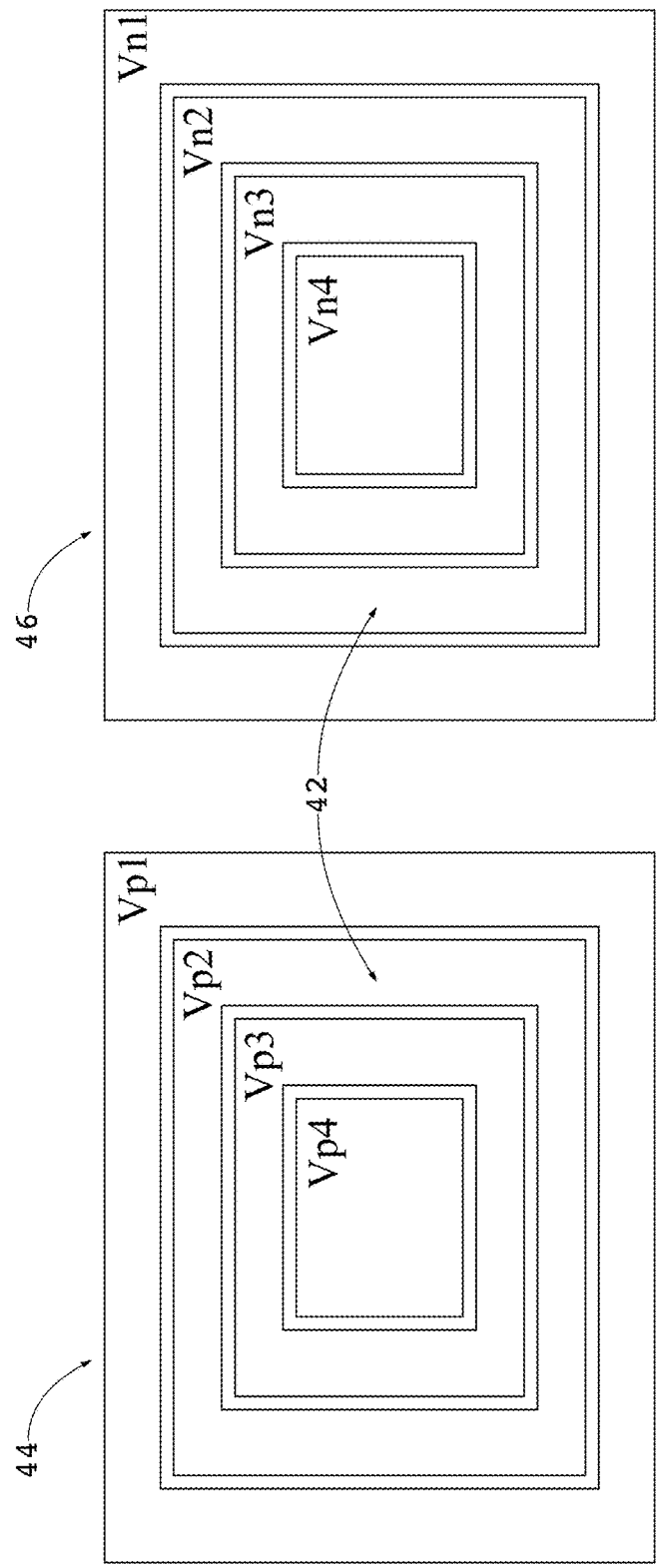
FIG. 10 illustrates one embodiment of adaptive electrode sensors of the present invention.

FIG. 10 illustrates one embodiment of adaptive electrode sensors of the present invention. In this example, each electrode of the adaptive sensor is made up of four capacitance segments 42 of helical shape. In one embodiment, a positive voltage can be applied to each of the capacitance segments of the source electrode 44 and a negative voltage can be applied to each of the capacitance segments of the detecting electrode 46. As discussed, different values of voltages applied to the capacitance segments (Vp1-Vp4; Vn1-Vn4) are used to steer the electric field and focus on a certain imaging region. In an adaptive ECVT sensor, the sensor is preferably comprised with a plurality of these electrodes, however the example simulation described here is shown using only two electrodes (one pair of source and detecting electrodes). It is appreciated that increasing the number of segments in the electrodes gives more flexibility in controlling electric field distribution. Although applied voltages are preferably time varying, they are depicted in the following examples as DC voltages for illustration purposes. For the following example illustrated with the example electrodes of FIG. 10, capacitance measurements are obtained using the capacitance measurement circuit of FIG. 19. As illustrated, capacitance measurements (Cx1-Cxn) are obtained between corresponding segments of the source and detecting electrodes (e.g., four pairs). Again, by obtaining the voltage measurement Vo, and applying the formula set forth in FIG. 8, the equivalent of the capacitances Cx1-Cx4 can be obtained. This data is then used to reconstruct the image for a multiphase flow between the adaptive sensors.

Figure 11:
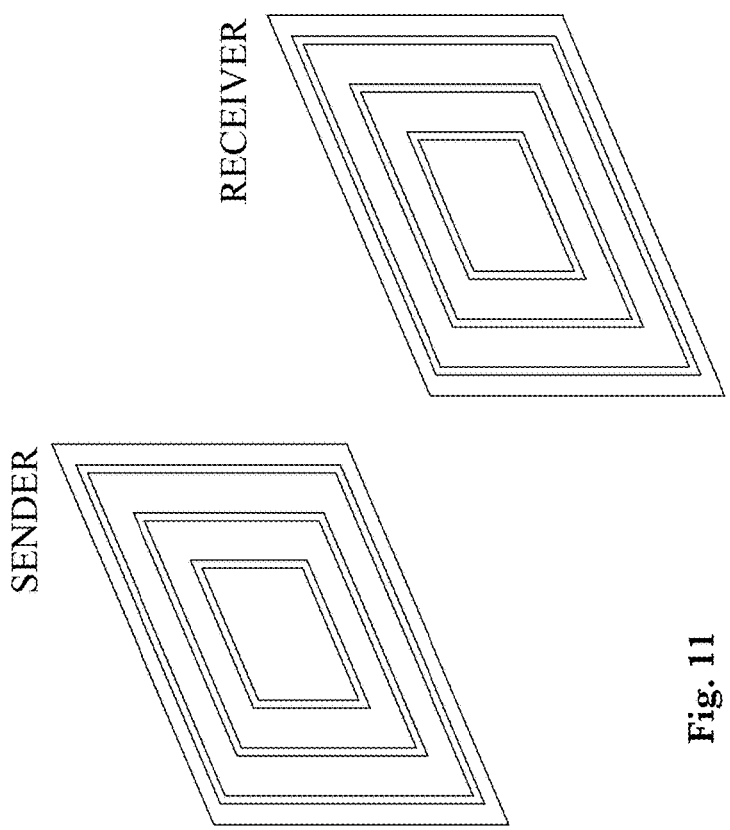
FIG. 11 illustrates one embodiment of adaptive electrode sensors shown in one example arrangement.

FIG. 11 illustrates one embodiment of adaptive electrode sensors of FIG. 10 shown in one example arrangement. Two different cases are explored:

Case 1:
  Vp1=Vp2=Vp3=Vp4=Vp5=+5 volts;
  Vn1=Vn2=Vn3=Vn4=−5 volts.
Case 2:
  Vp1=+1 v, Vp2=+2 v, Vp3=+4 v, Vp4=+7 v;
  Vn1==1 v, Vn2=−2 v, Vn3=−4 v, Vn4=−7 v.

Figure 19:
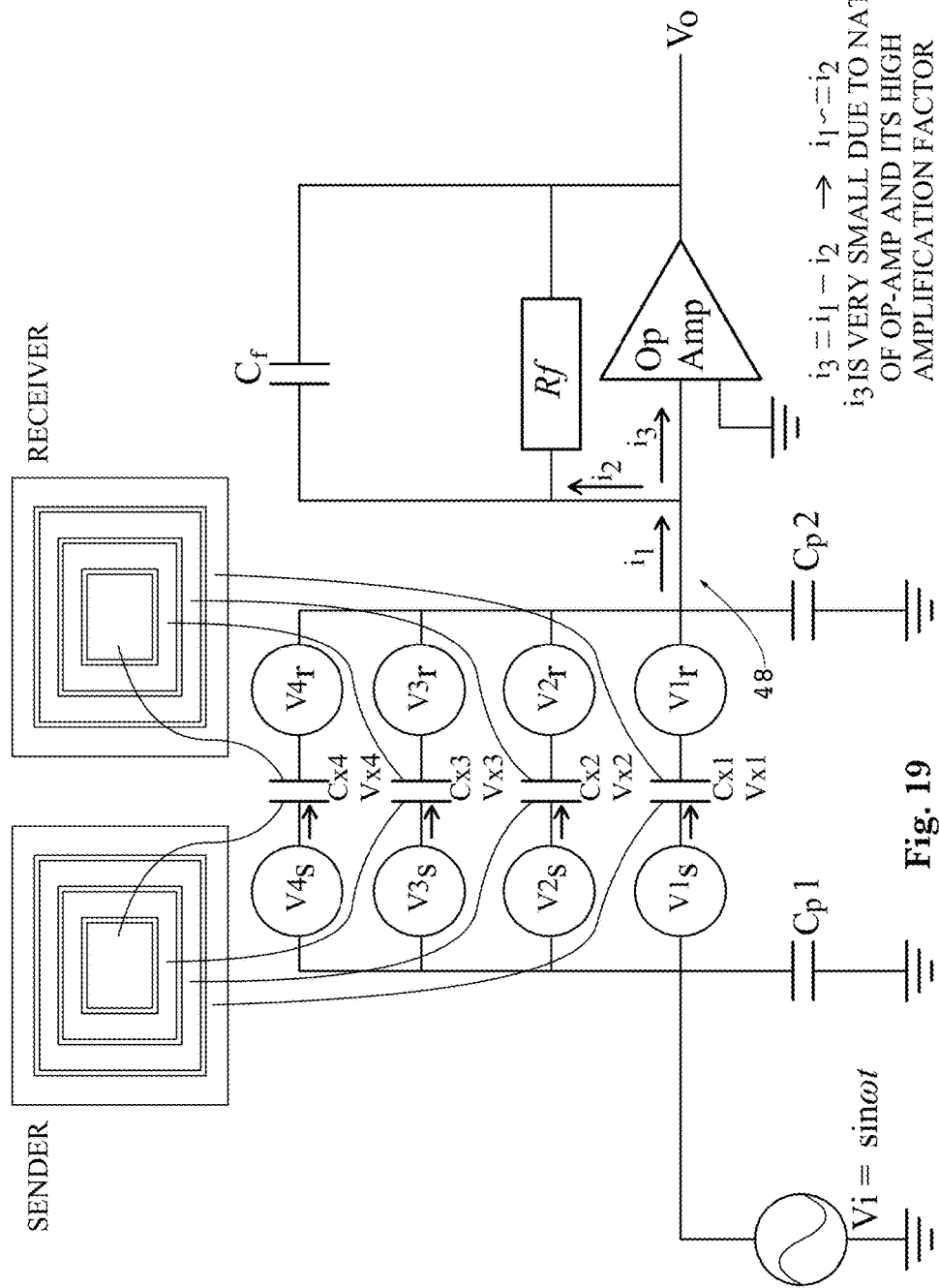
FIG. 19 illustrates an example embodiment of a capacitance measuring circuit for adaptive sensors of the present invention.

With reference to FIG. 19, when these voltages are applied, the voltage differences (Vx1-Vxn) between each corresponding segment causes currents to flow in proportion to the voltage difference and capacitance (Cx1-Cx4) of each segment pair. Accordingly, because largest applied voltages in this example are applied to the center capacitance segment of the electrodes, the largest current will most likely flow from Cx4. Each of the currents flowing from the capacitance segments are combined to form I1 shown generally at 48. In the preferred embodiment, a small portion of current I1 will go to the operational amplifier (current I3) and the rest will flow to Rf and Cf (current I2). The output voltage Vo will be related to the values of Rf and Cf and the level of current. It is appreciated that changing the shape of the capacitance segments or changing the voltages applied, and the distributions thereof, the current and the output voltage will change accordingly.

As discussed, the electric field intensity, and therefore capacitance sensitivity, will be higher in the imaging region where the applied voltage difference is the greatest. In this example, the greatest voltage difference occurs between the center capacitance segments (Vx4). When an object is present between the activated source and detecting (i.e., sender and receiver, respectively) electrodes, the measure capacitance will change based on the relative electric field intensity at the object location. Accordingly, in this example, objects passing through the middle of the sensor will generate a greater change in capacitance due to the higher sensitivity. The change in capacitance due to the object will result in an increase in total current I1 in proportion to the change in capacitance levels. Because the output voltage Vo depends on total current I1, the output voltage will also change proportional to the change in current. This measured change in output voltage can be used to calculate the change in capacitance levels between the capacitance segments which are then used to reconstruct volume images of objects or materials between the sensors.

According to principles of the present invention, the electric field can be concentrated at a location where higher sensitivity is desired. The electric field can also be controlled toward smoother gradients for more accurate information.

FIGS. 12A and 12B illustrate top cross-sectional views of electric field distributions for two example embodiments. FIGS. 13A and 13B illustrate isosurface views of electric field distributions for two example embodiments at the 50 v/m level. FIGS. 14A and 14B illustrate isosurface views of electric field distributions for two example embodiments at the 75 v/m level. FIGS. 12-14 depict variation in electric field concentration resulting from applying different voltage levels to individual segments. In this particular example, electric field is more focused toward edges of plates and center of imaging region.

Figure 15:
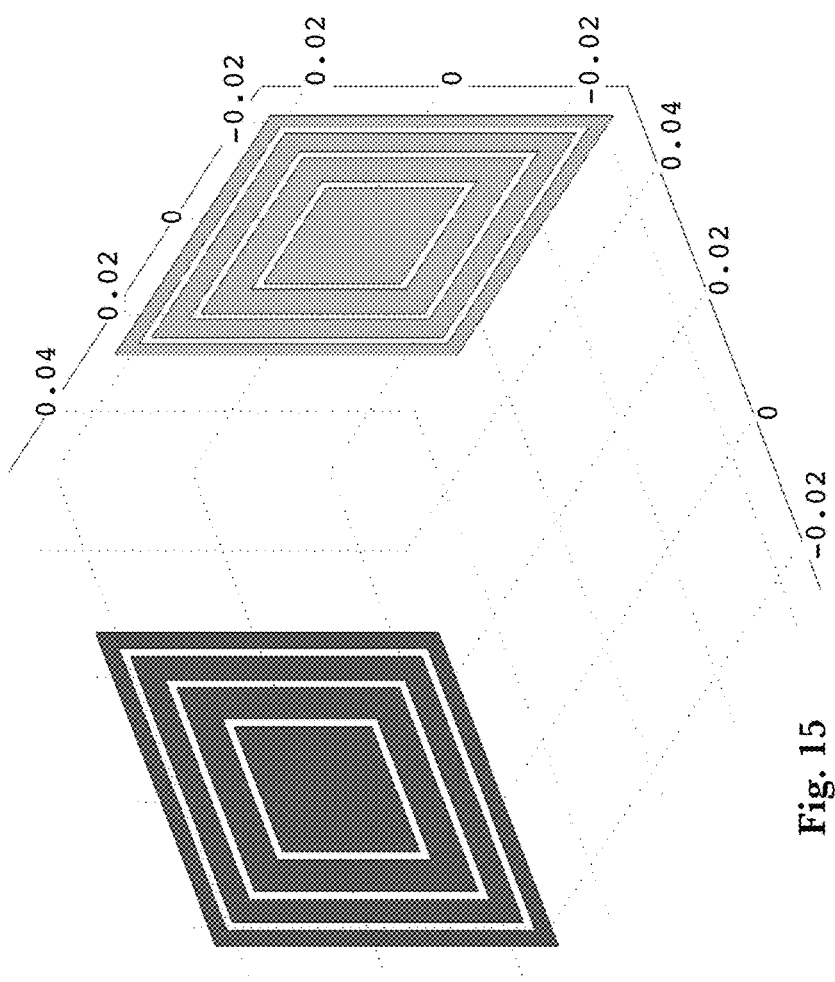
FIG. 15 illustrates another example arrangement of adaptive sensor plates of the present invention.

FIG. 15 illustrates another example arrangement of adaptive sensor electrodes of the present invention. In this example the electrodes are placed in adjacent to each other.

Case 3:
  Vp1=Vp2=Vp3=Vp4=Vp5=+5 volts;
  Vn1=Vn2=Vn3=Vn4=−5 volts.
Case 4:
  Vp1=+1 v, Vp2=+3 v, Vp3=+5 v, Vp4=+7 v;
  Vn1==1 v, Vn2=−3 v, Vn3=−5 v, Vn4=−7 v.

Figures 16A, 16B:
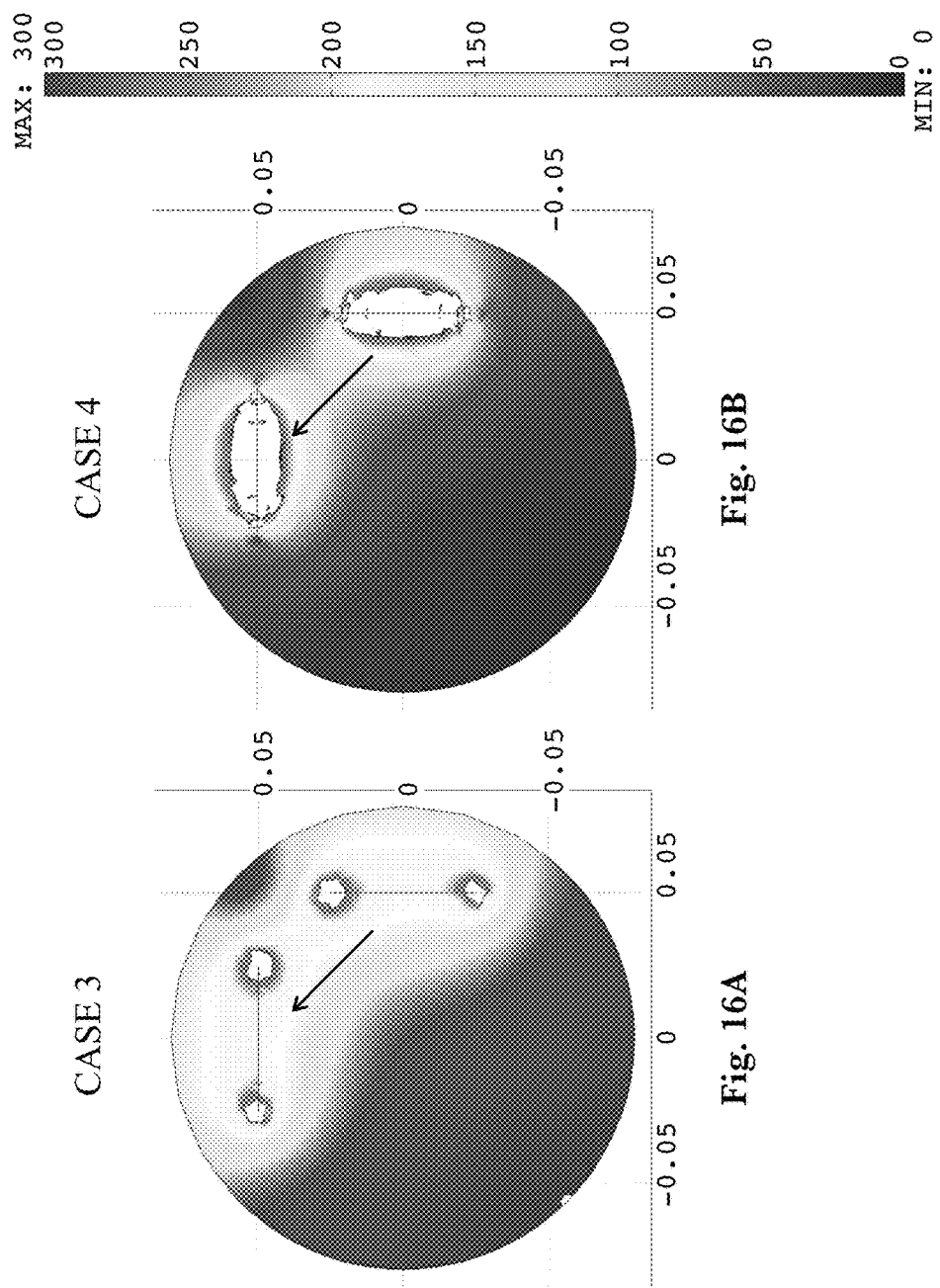
FIGS. 16A and 16B illustrate top cross-sectional views of electric field distributions for two additional example embodiments.

FIGS. 16A and 16B illustrate top cross-sectional views of electric field distributions for two additional example embodiments of FIG. 15. As illustrated the electric field gradient, moving between plates in the direction of the arrow, is more visible in Case 4.

Figures 17A, 17B:
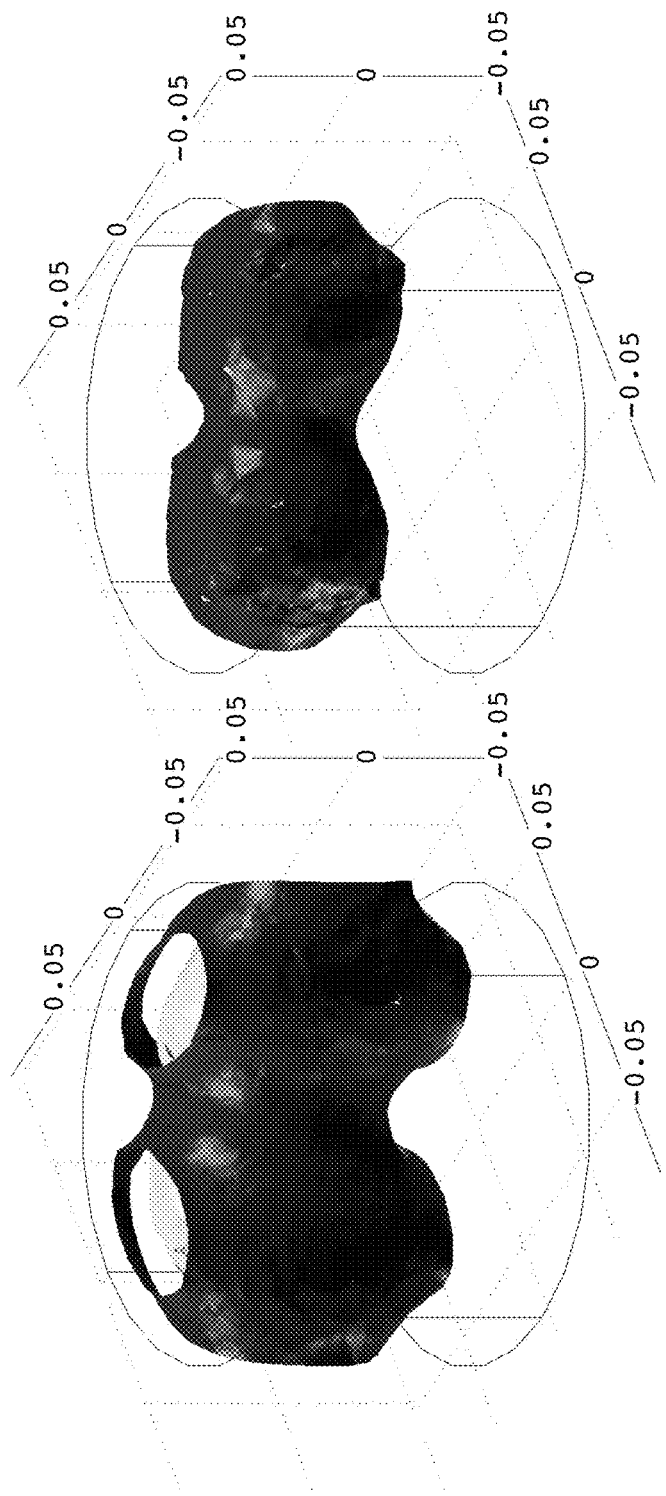
FIGS. 17A and 17B illustrate isosurface views of electric field distributions for two additional example embodiments at the 50 v/m level.
Figures 18A, 18B:
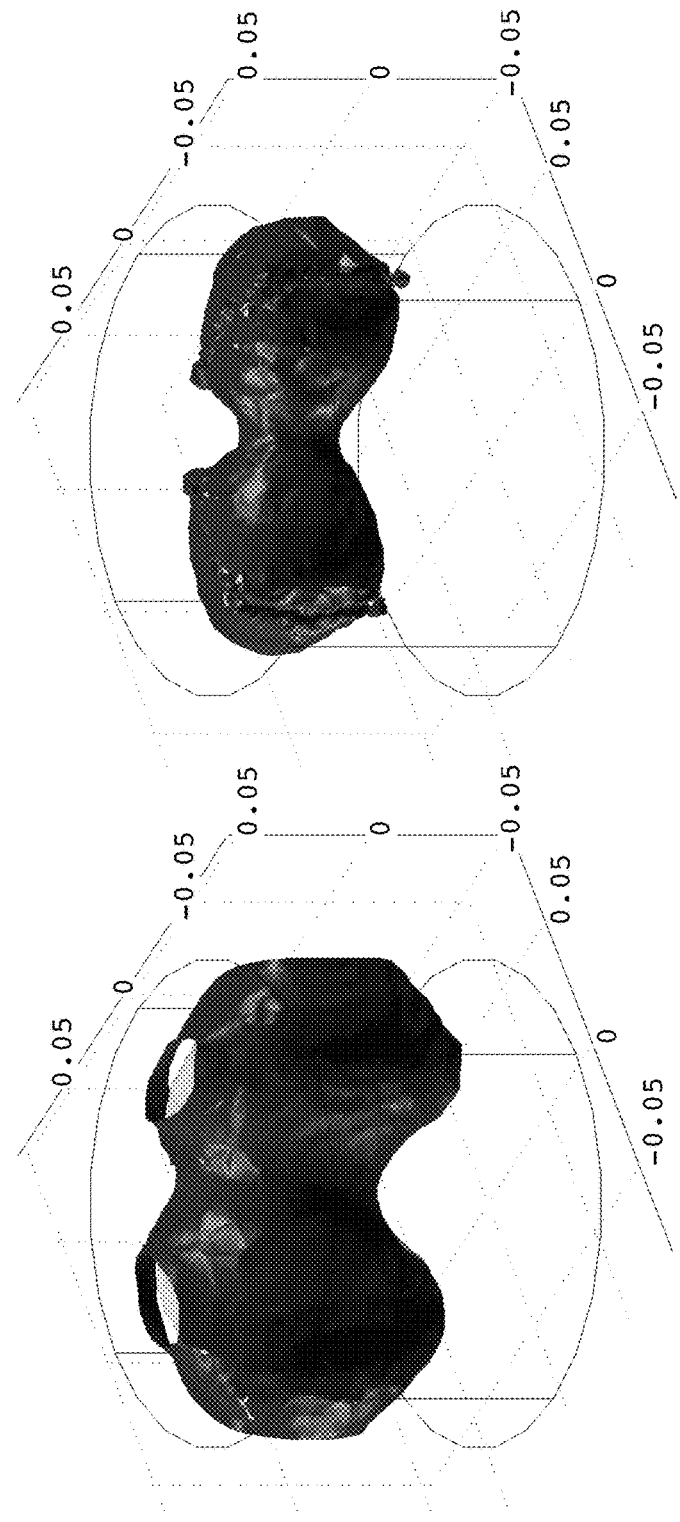
FIGS. 18A and 18B illustrate isosurface views of electric field distributions for two additional example embodiments at the 75 v/m level.

FIGS. 17A and 17B illustrate isosurface views of electric field distributions for two additional example embodiments at the 50 v/m level. FIGS. 18A and 18B illustrate isosurface views of electric field distributions for two additional example embodiments at the 75 v/m level. As illustrated, the figures illustrate that the electric field is more focused for Case 4.

Figure 32:
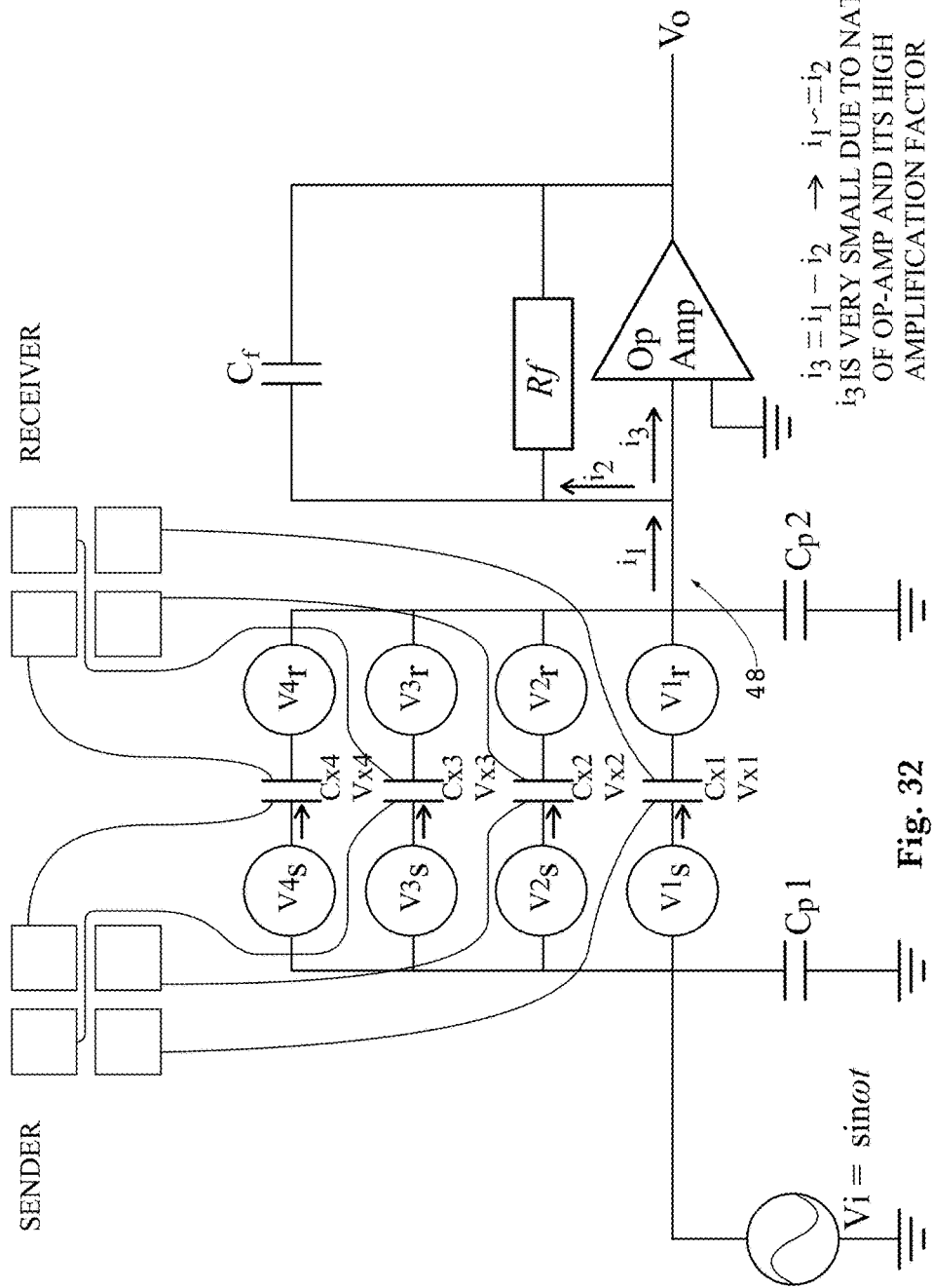
FIG. 32 illustrates another example embodiment of a capacitance measuring circuit for adaptive sensors of the present invention.

FIG. 19 and FIG. 32 illustrate example embodiments of a capacitance measuring circuit for adaptive sensors of the present invention as previously discussed. FIG. 20 illustrates an example embodiment of capacitance plates activated by different voltages levels through voltage dividers.

Figure 21:
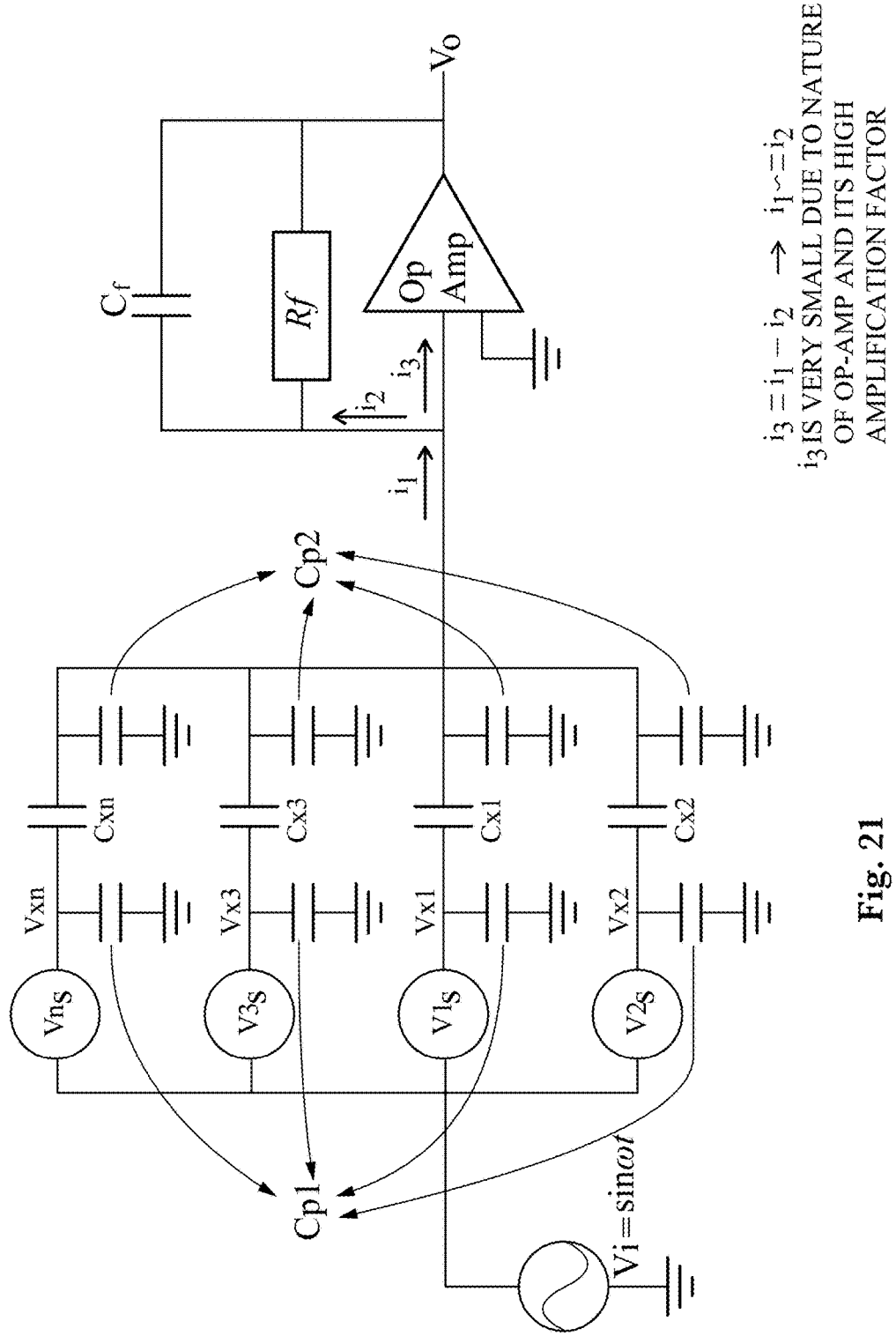
FIG. 21 illustrates an example circuit design when voltage control is in an acquisition box.

FIG. 21 depicts an example circuit design when voltage control is from an acquisition box, before connecting cables to the sensor segments. Typically, when measuring capacitance for tomography imaging, the variation in the signal due to change in material density or distribution in the imaging domain is measured. Usually the range of this change is minimal compared to static capacitance that exist in the system. In order to focus the measuring circuit on that varying component only (yielding accurate measurements), it is preferable to eliminate any static capacitance that is often referred to as "Parasitic capacitance". Without eliminating it, the resolution of the circuit will typically be stretched over a very wide range, instead of being focused on that small variable part. Cables that connect the circuit to the sensors are a major component of this static "parasitic capacitance". The circuit of FIG. 21 is different in the sense that it includes vertical branches of capacitance (Cp1 and Cp2 that are static capacitance mainly introduced by cables) after the voltage sources of individual segments. Accordingly, controlling voltages for each segment happen before the cable (at the main circuit or acquisition box location). The circuit as it is structured, automatically eliminates most of the static capacitance and the output voltage depends on Cx without regard to Cp1 or Cp2.

Figure 33:
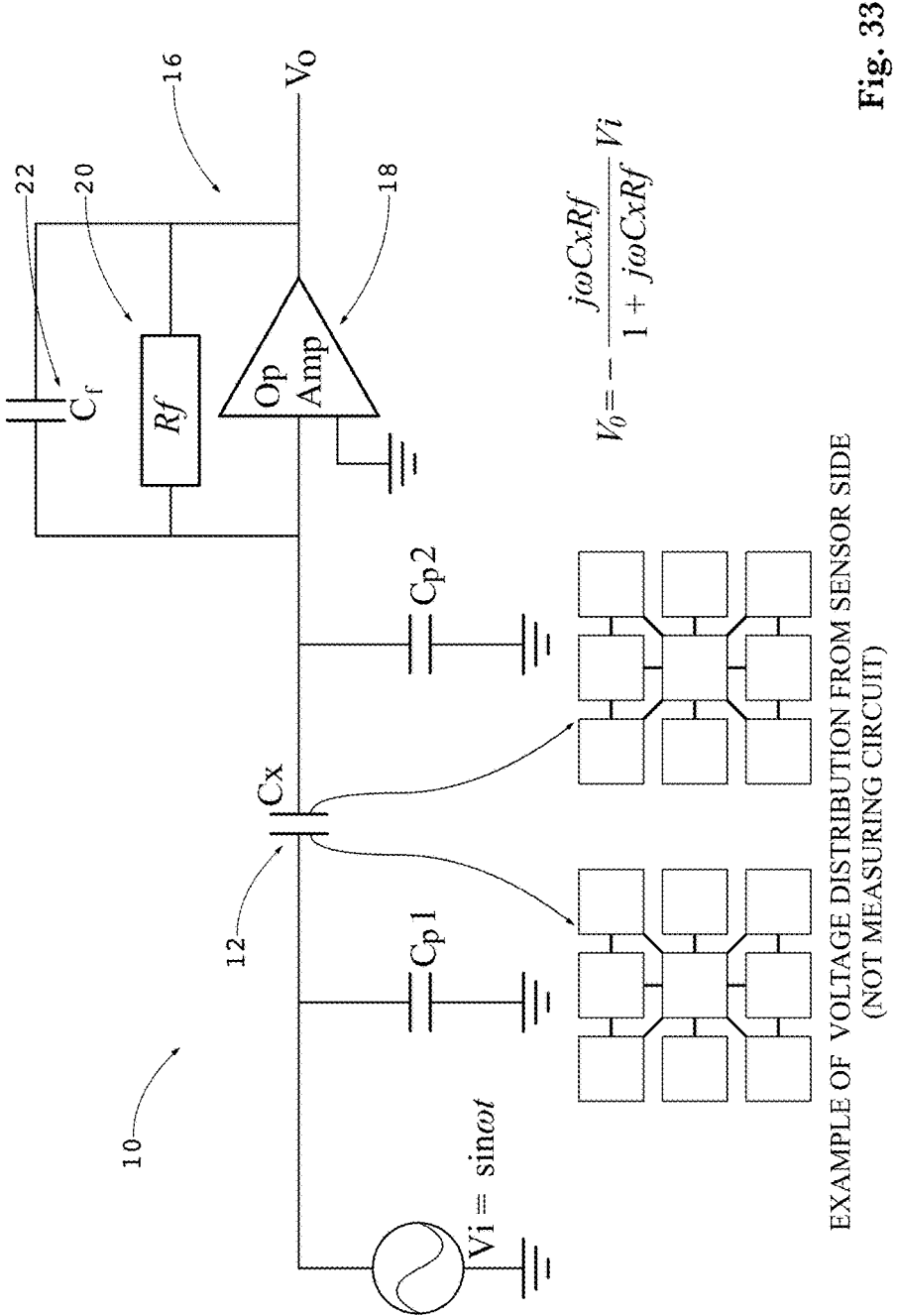
FIG. 33 illustrates an example circuit design when voltage control is in adaptive sensor side or when the voltage is distributed using components out of the acquisition box and where a conventional measuring circuit can be used to acquire capacitance signals of the adaptive sensor.

FIG. 33 illustrates an example circuit design when voltage control is in adaptive sensor side. In such an arrangement, a conventional measuring circuit may be used to measure adaptive capacitance. Voltage distribution on segments and adaptive capacitance value are determined by passive or active elements connected to the plate segments, preferably outside of the acquisition box. FIG. 34 illustrates an example circuit design with its equivalent representation when voltage control is in adaptive sensor side. Voltage division is based on total capacitance for each segment Ci_total (including parasitic) and R:
For Ri1+Ri2>>jwCxi and Ri1+Ri2~=1/jwCi_total:
i=Vi(jwCi_total)/(1+RjwCi_total)
Vxi=i/jwCxi, voltage is stable for Cxi>>Ci_total
The equivalent circuit representations relate the capacitance measured by a conventional circuit to the total capacitance of an adaptive sensor when voltage distribution is achieved outside the box.

Figure 35:
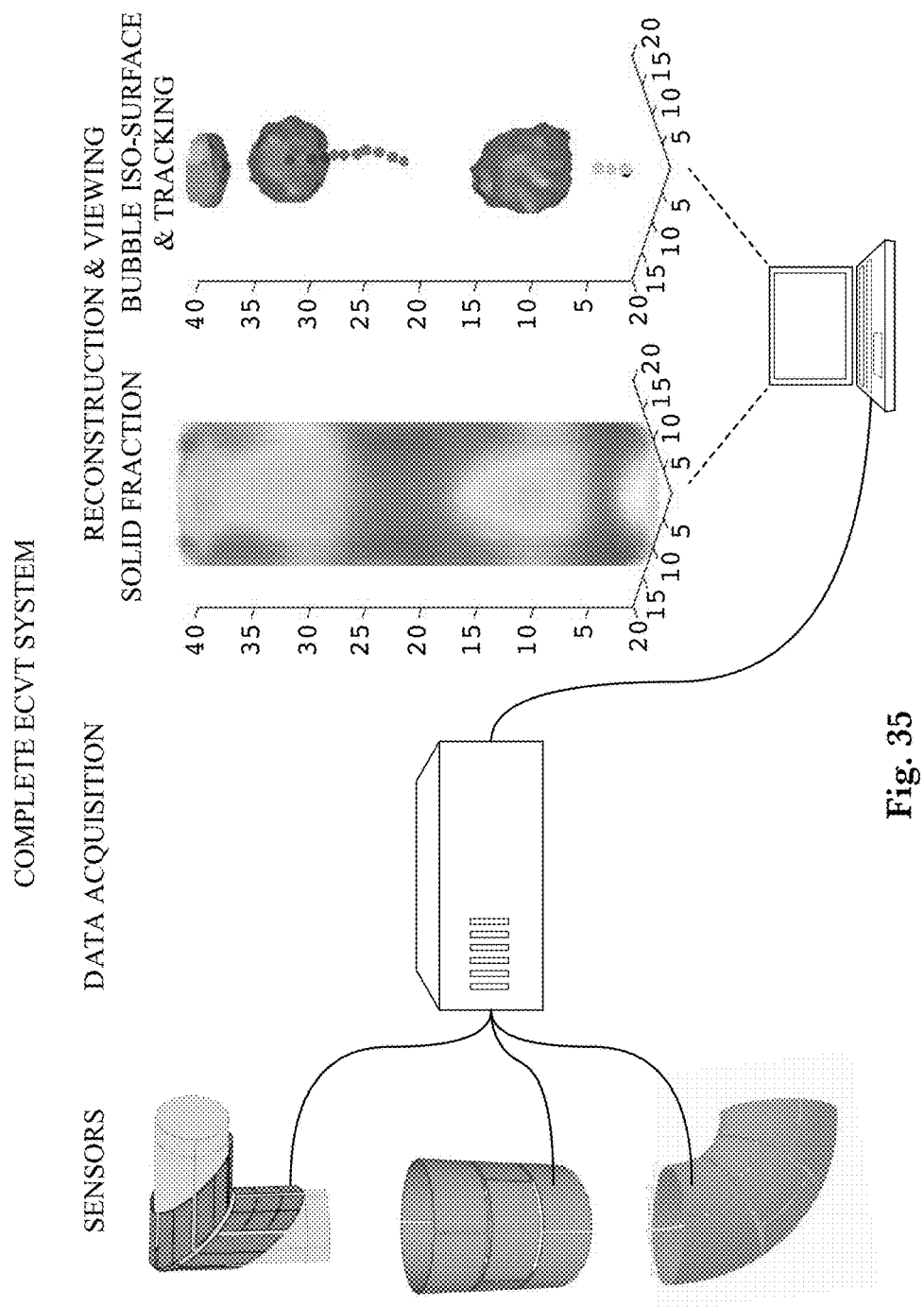
FIG. 35 illustrates an example diagram of a ECVT system.

FIG. 35 illustrates an example diagram of an ECVT system.

While certain embodiments of the present invention are described in detail above, the scope of the invention is not to be considered limited by such disclosure, and modifications are possible without departing from the spirit of the invention as evidenced by the following claims:

What is claimed is:
1. A system for tomographic imaging of a domain in a pipe, tube or object, the system comprising:
  a sensor, comprising:
    a plurality of electrodes configured to be placed around the pipe, tube or object, each electrode comprising a plurality of capacitance plate segments; and
  a voltage source;
  a measurement circuit electrically coupled to the sensor;
  wherein the plurality of electrodes is comprised of: a first electrode, having a plurality of capacitance plate segments that are addressable with the voltage source; a second electrode, having a plurality of capacitance plate segments, the capacitance plate segments of the second electrode electrically coupled to the measurement circuit; and wherein the capacitance plate segments of the first electrode form capacitance pairs with at least one of the capacitance plate segments of the second electrode when activated;
  and wherein the system is adapted to collect capacitance data by:
    defining a capacitor by using a capacitance plate segment on the first electrode as a source electrode, using a capacitance plate segment on the second electrode as a detecting electrode,
    charging and discharging the defined capacitor by directing a predetermined voltage to the source electrode from the voltage source;
    detecting a capacitance of the defined capacitor by detecting a current induced in the detecting electrode;
  an image reconstruction processor, in communication with the measurement circuit, wherein the image reconstruction processors is adapted to convert detected capacitance data into an image; and
  wherein the system is adapted to activate various combinations of electrodes with different voltage distributions or envelopes to provide control of system sensitivity.

2. The system of claim 1, wherein the measurement circuit is adapted to receive current from a plurality of the capacitance pairs of the first and second electrodes and convert it to an output voltage (Vo).

3. The system of claim 2, wherein the image reconstruction processor is programmed with one or more software routines executing on the processor to determine volume images from the output voltage (Vo).

4. The system of claim 1, wherein the measurement circuit is comprised of:
  an operational amplifier circuit adapted to receive current from a plurality of the capacitance pairs of the first and second electrodes and convert it to an output voltage (Vo).

5. The system of claim 4, wherein the output voltage (Vo) is a signal having an amplitude, phase, and frequency and wherein the processor is programmed with one or more software routines executing on the processor to determine the capacitance between the first and second electrodes.

6. The system of claim 1, further comprising a plurality of switches electrically connected to the voltage source and the plurality of capacitance plate segments of the first electrode for selectively activating each of the plurality of capacitance plate segments of the first electrode.

7. The system of claim 1, wherein the system is adapted to control the sensitivity of the sensor by changing the frequency of the voltage distribution applied to at least one electrode.

8. The system of claim 1, wherein the system is adapted to activate one electrode at a time as a source electrode and one electrode as the detecting electrode, and wherein the detecting electrode is connected to the measurement circuit.

9. The system of claim 1, wherein the image reconstruction processor is adapted to obtain the capacitance between all the electrodes and reconstruct an image of the region between the electrodes based on the capacitances obtained.

10. The system of claim 1, wherein a switch controlled by the measurement circuit selectively connects each capacitance plate segment of each electrode to the voltage source.

11. The system of claim 1, wherein the system is adapted to focus the electric field between the first and second electrodes by means of the voltage levels used to address the capacitance plate segments.

12. The system of claim 1, wherein sensor sensitivity is controlled by varying the voltage distribution or envelope applied to the capacitance plate segments.

13. The system of claim 1, wherein the electric field between electrodes of the sensor is focused toward the center of the electrodes by connecting voltages of various amplitudes to the capacitance plate segments of at least one of the electrodes, and wherein the voltages connected towards the center of the electrode is greater than the voltages connected to the periphery of the electrode.

14. The system of claim 1, wherein the sensor is adapted to be placed around a body of a human or animal to detect fluid flow or tissues through the body of the human or animal.

15. The system of claim 1, wherein the measurement circuit is adapted to receive current from all of the capacitance pairs of the first and second electrodes and convert it to an output voltage (Vo);
wherein the processor is programmed with one or more software routines executing on the processor to determine images from the output voltage (Vo);
wherein each of the capacitance plate segments of each of the first electrode are individually addressable by voltages and where sensor sensitivity is controlled by varying the voltage distribution or envelope applied to the capacitance plate segments of the first electrode.

16. The system of claim 1, wherein the system is adapted to allow control of sensitivity of the system by changing the phase of the voltage distribution applied to the first electrode.

17. The system of claim 1, wherein an envelope shape applied to the first electrode can be a combination of different envelopes to control steering or focus of system sensitivity toward a desired region.

18. The system of claim 1, wherein the system is adapted to allow for an increase in the number of independent capacitance measurements by using different envelopes for activating electrodes, and wherein each envelope has a different sensitivity distribution.

19. The system of claim 1, wherein the system is adapted to allow for an increase in the number of independent capacitance measurements by selecting different capacitance plate segments of an electrode to activate each time a capacitance measurement is acquired.

20. The system of claim 1, wherein the physical dimensions of the sensor are increased by adding electrodes or capacitance plate segments to the sensor.

21. The system of claim 1, wherein all the capacitance plate segments of the second electrode are electrically coupled to the measurement circuit.

22. A system for tomographic imaging of a domain in a pipe, tube or object, the system comprising:
a sensor, comprising:
a plurality of electrodes configured to be placed around the pipe, tube or object, each electrode comprising a plurality of capacitance plate segments; and
a voltage source;
a measurement circuit electrically coupled to the sensor;
wherein the plurality of electrodes is comprised of: a first electrode, having a plurality of capacitance plate segments that are addressable with the voltage source; a second electrode, having a plurality of capacitance plate segments, the capacitance plate segments of the second electrode electrically coupled to the measurement circuit; and wherein the capacitance plate segments of the first electrode form capacitance pairs with at least one of the capacitance plate segments of the second electrode when activated;
and wherein the system is adapted to collect capacitance data by:
defining a capacitor by using a capacitance plate segment on the first electrode as a source electrode, using a capacitance plate segment on the second electrode as a detecting electrode,
charging and discharging the defined capacitor by directing a predetermined voltage to the source electrode from the voltage source;
detecting a capacitance of the defined capacitor by detecting a current induced in the detecting electrode;
an image reconstruction processor, in communication with the measurement circuit, wherein the image reconstruction processors is adapted to convert detected capacitance data into an image; and
wherein the measurement circuit is adapted to receive current from all of the capacitance pairs of the first and second electrodes and convert it to an output voltage (Vo);
wherein the image reconstruction processor is programmed with one or more software routines executing on the processor to determine images from the output voltage (Vo);
wherein each of the capacitance plate segments of each of the first electrode are individually addressable by voltages and where sensor sensitivity is controlled by varying the voltage distribution or envelope applied to the capacitance plate segments of the first electrode; and
wherein the system is adapted to activate various combinations of electrodes with different voltage distributions or envelopes to provide control of system sensitivity.

23. A system for tomographic imaging of a domain in a pipe, tube or object, the system comprising:
a sensor, comprising:
a plurality of electrodes configured to be placed around the pipe, tube or object, each electrode comprising a plurality of capacitance plate segments; and
a current source;
a measurement circuit electrically coupled to the sensor;

wherein the plurality of electrodes is comprised of: a first electrode, having a plurality of capacitance plate segments that are addressable with the current source; a second electrode, having a plurality of capacitance plate segments, the capacitance plate segments of the second electrode electrically coupled to the measurement circuit; and wherein the capacitance plate segments of the first electrode form capacitance pairs with at least one of the capacitance plate segments of the second electrode when activated;

and wherein the system is adapted to collect capacitance data by:

defining a capacitor by using a capacitance plate segment on the first electrode as a source electrode, using a capacitance plate segment on the second electrode as a detecting electrode, charging and discharging the defined capacitor by directing a predetermined current to the source electrode from the current source;

detecting a capacitance of the defined capacitor by detecting a current induced in the detecting electrode;

an image reconstruction processor, in communication with the measurement circuit, wherein the image reconstruction processors is adapted to convert detected capacitance data into an image; and wherein the system is adapted to activate various combinations of electrodes with different voltage distributions or envelopes to provide control of system sensitivity.

24. The system of claim 23, wherein the measurement circuit is adapted to receive current from a plurality of the capacitance pairs of the first and second electrodes and convert it to an output voltage (Vo).

25. The system of claim 24, wherein the image reconstruction processor is programmed with one or more software routines executing on the processor to determine volume images from the output voltage (Vo).

26. The system of claim 23, wherein the measurement circuit is comprised of:

an operational amplifier circuit adapted to receive current from a plurality of the capacitance pairs of the first and second electrodes and convert it to an output voltage (Vo).

27. The system of claim 26, wherein the output voltage (Vo) is a signal having an amplitude, phase, and frequency and wherein the processor is programmed with one or more software routines executing on the processor to determine the capacitance between the first and second electrodes.

28. The system of claim 23, further comprising a plurality of switches electrically connected to the current source and the plurality of capacitance plate segments of the first electrode for selectively activating each of the plurality of capacitance plate segments of the first electrode.

29. The system of claim 23, wherein the system is adapted to control the sensitivity of the sensor by changing the frequency of the voltage distribution applied to at least one electrode.

* * * * *